(12) United States Patent
Shigdar

(10) Patent No.: US 10,577,610 B2
(45) Date of Patent: Mar. 3, 2020

(54) EPCAM APTAMERS AND CONJUGATES THEREOF

(71) Applicant: Deakin University, Warun Ponds (AU)

(72) Inventor: Sarah Shigdar, Warun Ponds (AU)

(73) Assignee: Deakin University, Waurun Ponds (AU)

( * ) Notice: Subject to any disclaimer, the term of this patent is extended or adjusted under 35 U.S.C. 154(b) by 51 days.

(21) Appl. No.: 15/550,671

(22) PCT Filed: Feb. 11, 2016

(86) PCT No.: PCT/AU2016/050085
§ 371 (c)(1),
(2) Date: Aug. 11, 2017

(87) PCT Pub. No.: WO2016/127216
PCT Pub. Date: Aug. 18, 2016

(65) Prior Publication Data
US 2018/0037892 A1 Feb. 8, 2018

(30) Foreign Application Priority Data

Feb. 11, 2015 (AU) .............................. 2015900437

(51) Int. Cl.
*C12N 15/11* (2006.01)
*C12N 15/115* (2010.01)
*A61K 31/7088* (2006.01)
*A61K 48/00* (2006.01)

(52) U.S. Cl.
CPC ........ *C12N 15/115* (2013.01); *A61K 31/7088* (2013.01); *A61K 48/00* (2013.01); *C12N 2310/16* (2013.01); *C12N 2310/3519* (2013.01); *C12N 2310/51* (2013.01)

(58) Field of Classification Search
None
See application file for complete search history.

(56) References Cited

U.S. PATENT DOCUMENTS 7,998,940 B2 8/2011 Diener et al.
2007/0178451 A1* 8/2007 Deng .................. C07K 14/405
435/6.15

FOREIGN PATENT DOCUMENTS

| CN | 103387988 | | 11/2013 |
|---|---|---|---|
| CN | 103409427 | A | 11/2013 |
| WO | WO-2007/137117 | A2 | 11/2007 |
| WO | WO-2010/023327 | A2 | 3/2010 |
| WO | WO-2013/003898 | A1 | 1/2013 |
| WO | WO-2013/163303 | A2 | 10/2013 |
| WO | WO-2014/019024 | A1 | 2/2014 |
| WO | WO-2014/019025 | A1 | 2/2014 |
| WO | WO 2014/068408 | | 5/2014 |
| WO | WO 2014/197455 | | 12/2014 |

OTHER PUBLICATIONS

Cimino et al, Epithelial cell adhesion molecule (EpCAM) is overexpressed in breast cancer metastases, Breast Cancer Res Treat, 2010, 123: 701-708 (Year: 2010).*
Hu et al, "Inhibition of Monocyte Adhesion to Brain-Derived Endothelial Cells by Dual Functional RNA Chimeras", 2014, Molecular Therapy—Nucleic Acids, vol. 3, e209.
Mu et al, "Solubilization of flurbiprofen into aptamer-modified PEG-PLA micelles for targeted delivery to brain-derived endothelial cells in vitro", 2013, Journal of Microencapsulation, vol. 30, No. 7.
Supplementary Examination Report dated Nov. 6, 2018 issued in corresponding European Patent Application No. 16748486.
Bagalkot et al "An Aptamer-Doxorubicin Physical Conjugate as a Novel Targeted Drug-Delivery Platform" Angewandte Chemie vol. 45, pp. 1-5, 2006.
Cerchia et al "Nucleic Acid Aptamers in Cancer Medicine" FEBS Letters vol. 528, pp. 12-16, 2002.
Chen et al "Aptamer-Based Endocytosis of a Lysosomal Enzyme" PNAS vol. 105, pp. 15908-15913, 2008.
Cibiel et al "Methods to Identify Aptamers Against Cell Surface Biomarkers" Pharmaceuticals vol. 4, pp. 1216-1235, 2011.
Imrich et al "EpCAM and Its Potential Role in Tumor-Initiating Cells" Cell Adhesion and Migration vol. 6, pp. 30-38, 2012.
Kanwar et al "Chimeric Aptamers in Cancer Cell-Targeted Drug Delivery" Critical Reviews in Biochemistry and Molecular Biology vol. 46, pp. 459-477, 2011.
Li et al "Epithelial Cell Adhesion Molecule Aptamer Functionalized PLGA-Lecithin-Curcumin-PEG Nanoparticles for Targeted Drug Delivery to Human Colorectal Adenocarcinoma Cells" International Journal of Nanomedicine vol. 9, pp. 1083-1096, 2014.
Macdonald et al "Development of a Bifunctional Aptamer Targeting the Transferrin Receptor and Epithelial Cell Adhesion Molecule (EpCAM) for the Treatment of Brain Cancer Metastases" ACS Chemical Neuroscience vol. 8, pp. 777-784, 2017.
Macdonald et al "Targeting Triple Negative Brain Cancer Metastases" Lorne Cancer Conference, 2014.
Macdonald et al "Truncation and Mutation of a Transferrin Receptor Aptamer Enhances Binding Affinity" Nucleic Acid Therapeutics vol. 26, pp. 348-354, 2016.
Shigdar et al "Aptamers as Theranostic Agents: Modifications, Serum Stability and Functionalisation" Sensors vol. 13, pp. 13624-13637, 2013.
Shigdar et al "RNA Aptamer Against a Cancer Stem Cell Marker Epithelial Cell Adhesion Molecule" Cancer Science vol. 102, pp. 991-998, 2011.
Shigdar et al "RNA Aptamers Targeting Cancer Stem Cell Marker CD133" Cancer Letters vol. 330, pp. 84-95, 2013.

(Continued)

*Primary Examiner* — Ekaterina Poliakova-Georgantas
(74) *Attorney, Agent, or Firm* — Cesari and McKenna, LLP

(57) ABSTRACT

The present disclosure relates to an EpCAM aptamer or an EpCAM aptamer conjugate having bi-functional activity and to uses thereof. In particular, the present disclosure also relates to an aptamer conjugate which binds to the transferrin receptor (TfR) and EpCAM which is useful for treatment of brain tumours and/or brain metastasis.

14 Claims, 20 Drawing Sheets
Specification includes a Sequence Listing.

(56) References Cited

OTHER PUBLICATIONS

Wang et al "Evaluation of CD44 and CD133 as Cancer Stem Cell Markers for Colorectal Cancer" Oncology Reports vol. 28, pp. 1301-1308, 2012.

Went et al "Frequent EpCAM Protein Expression in Human Carcinomas" Human Pathology vol. 35, pp. 122-128, 2004.

Yeung et al "Cancer Stem Cells from Colorectal Cancer-Derived Cell Lines" PNAS vol. 107, pp. 3722-3727, 2010.

Baeuerle, et al., "EpCAM (CD326) finding its role in cancer", British Journal of Cancer, 2007, vol. 96, No. 3, pp. 417-423.

Imrich, et al.,"EpCAM and its potential role in tumor-initiating cells", Cell Adhesion & Migration, 2012, vol. 6, No. 1, pp. 30-38.

McConnell, et al., "Aptamers as promising molecular recognition elements for diagnostics and therapeutics in the central nervous system", Nucleic Acid Therapeutics, 2014, vol. 24, No. 6, pp. 388-404.

Song, et al., "Selection of DNA aptamers against epithelial cell adhesion molecule for cancer cell imaging and circulating tumor cell capture", Analytical Chemistry, 2013, vol. 85, No. 8, pp. 4141-4149.

\* cited by examiner

| | |
|---|---|
| 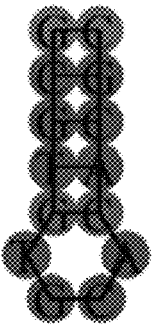 TfR1<br>5' GCG TGT GCA CAC GC 3' (SEQ ID NO:4) | 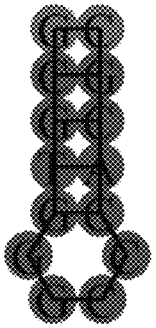 TfR2<br>5' GCG TGG GCC CAC GC 3' (SEQ ID NO:5) |
| 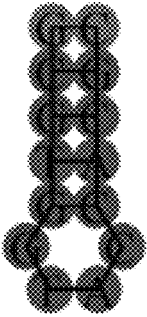 TfR3<br>5' GCG TGG TAC CAC GC 3' (SEQ ID NO:6) | 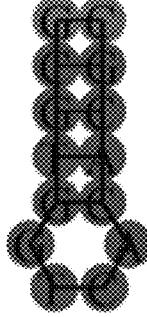 TfR4<br>5' GCG TGG TCA CAC GC 3' (SEQ ID NO:7) |
| 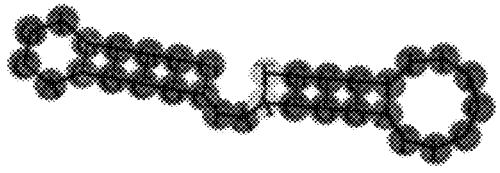 Bifunctional aptamer 1 (Bi1)<br>5' GCG CGT GCA CGC GCT AAC GGA TTC CTT TTC CGT 3' (SEQ ID NO:8) |  Bifunctional aptamer 2 (Bi2)<br>5' GCG CGG GCC CGC GCT AAC GGA GGT TGC GTC CGT 3' (SEQ ID NO:2) |
| 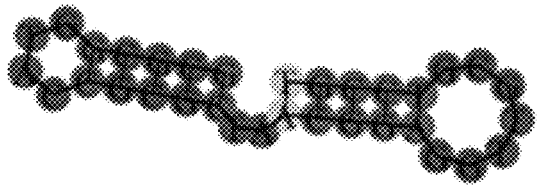 Bifunctional 3 (Bi3)<br>5' GCG CGG TAC CGC GCT AAC GGA GGT TGC GTC CGT 3' (SEQ ID NO:3) | 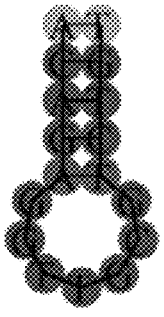 EpCAM aptamer (Ep7)<br>5' ACA GAG GTT GCG TCT GT 3'<br>(SEQ ID NO:9) |

FIG. 14A

EpCAM aptamer (Ep8)

5' CCC ACG TTG TCA TGG G 3'

(SEQ ID NO:11)

EpCAM aptamer (Ep9)

5' GGG GTT GGC CCC 3'

(SEQ ID NO:12)

Extended Ep7 aptamer (ExEp7)

5' CGC GCG CCG CAG GTT GCG TGC GGC GCG CG 3' (SEQ ID NO:13)

Scrambled extended Ep7 aptamer (ScrExEp7)

5' CGC GCG CCG CAT TCC TTT TGC GGC GCG CG 3' (SEQ ID NO:14)

EPCAM APTAMERS AND CONJUGATES THEREOF

This application is the National Stage of International Application No. PCT/AU2016/050085, filed on Feb. 11, 2016, which claims priority to Australian Application No. 2015900437, filed on Feb. 11, 2015. The contents of both applications are hereby incorporated by reference in their entirety.

RELATED APPLICATIONS AND INCORPORATION BY REFERENCE

All documents cited or referenced herein, together with any manufacturer's instructions, descriptions, product specifications and product sheets for any products mentioned herein or any document incorporated by reference herein, are hereby incorporated herein by reference in their entirety.

CROSS-REFERENCE

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

This application claims priority to AU 2015900437 filed 11 Feb. 2015, the entire contents of which are hereby incorporated by reference.

REFERENCE TO SEQUENCE LISTING

The entire content of the electronic submission of the sequence listing is incorporated by reference in its entirety for all purposes.

FIELD OF THE INVENTION

The present disclosure relates to EpCAM aptamers and EpCAM aptamer conjugates having bi-functional activity and to uses thereof. The aptamers and aptamer conjugates are useful for treatment of brain tumours and/or brain metastasis.

BACKGROUND OF THE INVENTION

In the developed world, cancer is currently the number one cause of death, primarily due to ageing populations. Survival rates are reduced for patients whose cancer undergoes metastasis to another site in the body and metastases to the brain have a particularly poor prognosis, with average survival being less than six months. It is estimated that brain metastases characterise 8.5-9.6% of all cancer diagnoses and are ten times more common than primary brain tumours, with most of these secondary tumours originating from primary lung, breast, skin (melanoma) and colorectal cancer, and malignant melanoma.

Like most cancers, treatment of brain metastasis involves three options; surgery, radiotherapy or chemotherapy. While these approaches can extend the survival of patients and improve quality of life, the prognosis for sufferers remains disheartening. Surgical resection has high rates of recurrence, and both chemotherapy and radiotherapy are non-specific and have poor safety profiles. Most chemotherapeutics are further complicated by the limited access of circulating drugs to the brain parenchyma. Temozolomide (TMZ) is one drug that can enter the brain, however it is still limited by a lack of efficacy (Minniti G et al, (2014) J Neurooncol 118(2):329-34). As such, there is a need for targeted drugs that can firstly enter the brain environment, but also limit their toxicity to cancer cells, and in particular the tumorigenic subpopulation.

The treatment of brain tumours is complicated by the presence of the blood-brain barrier (BBB), which isolates the brain microenvironment from the systemic circulation by strictly regulating the passage of molecules. As such, chemotherapeutic drugs are scarcely able to enter the brain, although they can still do damage elsewhere in the body.

Brain tumours as small as 1 mm can compromise the permeability of the BBB. However, this effect is not homogenous throughout the BBB, and as such, does little to improve the administration of sufficient quantities of drugs (Huse J T et al, (2010) Nature Reviews Cancer 10(5):319-31). One technique employed to avoid the problem presented by the BBB, direct cranial injection, is quite invasive and harmful (Lassaletta A et al, (2009) 95(1):65-9). While this approach has been shown to be effective, it carries the risk of infection and other side effects. Other methods involve increasing the permeability of the BBB through osmotic or chemical means. Again, these are risky treatment options, and have the potential to induce seizures and other neurological side effects.

The transferrin receptor 1 (TfR) is a membrane glycoprotein involved in iron homeostasis. It is expressed strongly on the surface of the BBB, as well as on many cancer cell lines (Wilner S E et al, Mol Ther Nucleic Acids 2012; 1:e21) and has been identified as an effective target for receptor-mediated transcytosis (RMT) of drug conjugates through the BBB. While the TfR is saturated in most cell types where it is expressed, such as red blood cells, hepatocytes, intestinal cells, macrophages and the brain itself, it is not saturated on the BBB, where its expression is considerably higher.

It has been proposed that the growth of cancers is driven by the presence of a unique subpopulation of cells with self-renewal properties. These cancer stem cells (CSC) are relatively quiescent and drug-resistant, and there is evidence suggesting that they may arise from normal stem cells or from epigenetic modifications resulting in the de-differentiation of other cells. Furthermore, it seems that inter-conversion is possible between CSCs and progenitor cells, which some have suggested can be characterised as a dynamic equilibrium.

The first line of evidence pointing to the existence of CSCs were studies involving the xenotransplantation of serial dilutions of cancer cells into immunodeficient mice. These have found that it takes a large number of cells to develop cancer in the animal model, suggesting that only some cells have the ability to do so.

Given the role that CSC play in tumour development, there is a need for novel targeted therapeutics that can be directed towards specifically eliminating this population of cells (which can be refractory to treatment with conventional therapy) in addition to the tumour, and which further are capable of crossing the BBB to treat brain tumours and brain metastasis, including inoperable brain tumours.

SUMMARY OF THE INVENTION

The effectiveness of antibodies in the treatment of brain tumours is hampered by their size thus compromising their ability to pass the blood brain barrier (BBB). Because aptamers are significantly smaller in size compared with antibodies, and lack non-specific Fc-mediated effects which can compromise antibody therapy, they are particularly advantageous over antibodies for cancer therapy. The present disclosure is directed to bi-functional aptamers which can effectively target brain metastases and/or brain tumours.

The present disclosure describes an EpCAM aptamer which binds to EpCAM as well as an EpCAM aptamer conjugate which exhibits dual functionality of being able to pass through the blood brain barrier and which binds to a marker present on tumour cells located within the brain. The aptamer or aptamer conjugate can be loaded with a chemotherapeutic agent which is delivered to the tumour resulting in tumour cell death. The aptamer conjugate is capable of entering the brain via receptor-mediated transcytosis (RMT) and binding to a cancer stem cell marker expressed by a brain tumour or brain metastasis. In a particular example, the aptamer conjugate binds to EpCAM and to the transferrin receptor (TfR). The aptamer conjugate may be RNA or DNA or a combination of RNA and DNA. In one example, the aptamer conjugate binds to human EpCAM. In a further example, the aptamer conjugate binds to human TfR. In a further example, the aptamer conjugate specifically binds to EpCAM and specifically binds to the transferrin receptor (TfR). In another example, the aptamer conjugate binds to TfR independently of its binding to EpCAM and vice versa.

In one example, the aptamer conjugate is a fusion of two aptamer sequences (or 'binding portions' as described herein). In another example, the aptamer conjugate contains one aptamer sequence (or binding portion) linked to another aptamer sequence (or binding portion). Suitable linker sequences will be known in the art.

The aptamer or aptamer conjugate of the present disclosure may be synthetically generated. In another example the aptamer or aptamer conjugate is isolated or purified.

In one embodiment, the present disclosure provides an aptamer which binds to EpCAM comprising a loop region sequence selected from any one of (i) bases 5 to 13 of SEQ ID NO:9 (AGGTTGCGT), (ii) bases 4 to 13 of SEQ ID NO:11 (ACGTTGTCAT) or (iii) bases 4 to 9 of SEQ ID NO:12 (GTTGGC) and optionally one or more substitutions therein.

The aptamer may comprise one, two or three substitutions within the loop region sequence as specified above.

In one example, the aptamer comprises a loop region of bases 5 to 13 of SEQ ID NO:9 and a stem region comprising between 3 and 15 paired bases. In a further example, the aptamer comprises a stem region comprising between 4 and 10 paired bases. In a further example, the aptamer comprises a stem region comprising 10 paired bases. In a further example, the aptamer comprises a stem region comprising 4 paired bases.

In one example, the aptamer comprises or consists of the sequence set forth in SEQ ID NO:9. In one example, the aptamer comprises or consists of the sequence set forth in SEQ ID NO:13.

In one example, the aptamer comprises a loop region of bases 4 to 13 of SEQ ID NO:11 and a stem region comprising between 3 and 15 paired bases. In one example, the aptamer comprises between 3 and 5 paired bases. In another example the aptamer comprises 3 paired bases.

In one example, the aptamer comprises or consists of the sequence set forth in in SEQ ID NO:11.

In one example, the aptamer comprises a loop region of bases 4 to 9 of SEQ ID NO:12 and a stem region comprising between 3 and 15 paired bases. In one example, the aptamer comprises between 3 and 5 paired bases. In one example, the aptamer comprises a stem region of 3 paired bases.

In one example, the aptamer comprises or consists of the sequence set forth in in SEQ ID NO:12.

In one example, the aptamer has a binding affinity (KD) for EpCAM of about 1 nM to about 500 nM, of about 1 nm to about 400 nM, of about 3 nM to about 300 nM, of about 3 nM to about 150 nM, of about 3 nM to about 100 nM, of about 5 nM to about 100 nM, of about 5 nM to about 80 nM, of about 5 nM to about 50 nM, of about 8 nM to about 35 nM, of about 8 nM to about 10 nM, less than 10 nM, or less than 5 nM.

In another embodiment, the present disclosure provides an aptamer conjugate which binds to the transferrin receptor (TfR) and EpCAM. The aptamer conjugate may be RNA, DNA or a combination of RNA and DNA. The aptamer conjugate may bind TfR independently of binding to EpCAM.

In one example, the present disclosure provides an aptamer conjugate comprising a consensus sequence 5'-GCG CGG $X_1X_2$C CGC GCT AAC GGA GGT TGC GTC CGT-3' (SEQ ID NO:1) wherein the aptamer conjugate binds to EpCAM and TfR. In one example, $X_1$ and $X_2$ are A, T, C or G. In one example, $X_1$ is G or C and $X_2$ is A or T.

In one example, the present disclosure provides an aptamer conjugate comprising the sequence 5'-GCG CGG GCC CGC GCT AAC GGA GGT TGC GTC CGT-3' (SEQ ID NO:2) optionally having one or more substitutions therein, wherein the aptamer conjugate binds to EpCAM and TfR.

In another example, the present disclosure provides an aptamer conjugate comprising the sequence 5'-GCG CGG TAC CGC GCT AAC GGA GGT TGC GTC CGT-3' (SEQ ID NO:3) optionally having one or more substitutions therein, wherein the aptamer conjugate binds to EpCAM and TfR.

The present disclosure also provides an aptamer conjugate comprising the sequence 5'-GC GCG GTA C CG CGC TA ACG G AT TCC TTT T CC GT-3' (SEQ ID NO:10) optionally having one or more substitutions therein, wherein the aptamer conjugate binds to EpCAM and TfR.

In another example, the sequence according to SEQ ID NO:1, SEQ ID NO:2, SEQ ID NO:3 or SEQ ID 10 comprises least one, two, three, four, five, six, seven, eight, nine, ten, eleven, twelve, thirteen or fourteen substitutions therein. In another example, the one or more substitutions occur within the TfR binding portion of the aptamer conjugate. In another example, the sequence according to SEQ ID NO:1, SEQ ID NO:2, SEQ ID NO:3 or SEQ ID NO:10 comprises at least one, two, three, four, five, six, seven, or eight substitutions within a stem region of the aptamer conjugate. In another example, the at least one, two, three, four, five, six, seven or eight substitutions occur within the stem region of the TfR binding portion of the aptamer conjugate. In one example, the stem region is that of the predicted two dimensional structure of the aptamer conjugate.

In one example, the TfR binding portion does not compete with transferrin for binding to the transferrin receptor.

The inventors found that the binding affinities of the conjugate aptamers was not compromised and the binding affinities were typically similar, if not stronger compared to those of the single aptamers from which they were derived.

In one example, the aptamer conjugate of the present disclosure has a binding affinity ($K_D$) for TfR of about 300 to 340 nM. In another example, the aptamer conjugate of the present disclosure has a binding affinity for TfR of between 150 and 450 nM, between 200 and 420 nM, between 250 and 350 nM, between 270 and 340 nM, or between 300 and 340 nM. In one example, the binding affinity is measured on bEnd.3 cells.

In one example, the aptamer conjugate of the present disclosure has a binding affinity ($K_D$) for EpCAM of about 210 to 220 nM. In another example the aptamer conjugate of the present disclosure has a binding affinity for EpCAM of between 130 and 280 nM, between 150 and 260 nM, between 170 and 240 nM, or between 200 and 220 nM. In one example, the binding affinity is measured on HEY cells.

In one example, the aptamer conjugate comprises a sequence length of between 33 and 100 bases. In another example, the aptamer conjugate comprises a sequence of between 33 and 80 bases, between 33 and 70 bases, between 33 and 50 bases, or between 33 and 40 bases.

In another example, the aptamer conjugate comprises the sequence of SEQ ID NO:1, SEQ ID NO:2, SEQ ID NO:3, or SEQ ID NO:10 wherein the sequence length is between 33 and 100 bases. In another example, the sequence length is between 33 and 80 bases, between 33 and 70 bases, between 33 and 50 bases, or between 33 and 40 bases.

In another example, the aptamer conjugate consists essentially of the sequence of SEQ ID NO:1, SEQ ID NO:2, SEQ ID NO:3 or SEQ ID NO:10.

In another example, the aptamer conjugate consists of the sequence of SEQ ID NO:2, SEQ ID NO:3 or SEQ ID NO:10.

In another embodiment, the aptamer or aptamer conjugate comprises one or more modifications (modified aptamer) that improve aptamer stability (in vitro or in vivo). Suitable modifications are discussed elsewhere herein. In one example, the pyrimidine bases are 2'-fluor (2'-F) modified. In another example, the 3' end of the aptamer conjugate is modified to protect it from nuclease digestion. In another example, the aptamer conjugate is modified by coupling the 5' end to a fluorphore (e.g. Cy3, Cy5 or TYE 665). In another example the aptamer or aptamer conjugate comprises an inverted deoxythymidine (dT), designated inv-dT (reverse linkage) at the 3' end.

In another embodiment, the present disclosure also provides an aptamer or aptamer conjugate having substantially the same ability to bind to EpCAM as that of an aptamer comprising the sequence of SEQ ID NO:1, SEQ ID NO:2, SEQ ID NO:3, SEQ ID NO:9 SEQ ID NO:10, SEQ ID NO:11 or SEQ ID NO:12. In one example, 'having substantially the same ability to bind' means having substantially the same or similar binding affinity as the aptamer of SEQ ID NO:1, SEQ ID NO:2, SEQ ID NO:3, SEQ ID NO:9, SEQ ID NO:10, SEQ ID NO:11 or SEQ ID NO:12. In another example, 'having substantially the same ability to bind' means binding to the same or overlapping epitope as the aptamer of SEQ ID NO:1, SEQ ID NO:2, SEQ ID NO:3, SEQ ID NO:9, SEQ ID NO:10, SEQ ID NO:11 or SEQ ID NO:12.

In one example, the aptamer or aptamer conjugate specifically binds to EpCAM$^+$ cell(s).

In another example, the EpCAM+ cell(s) is a stem cell(s). In another example, the stem cell is an isolated cancer stem cell(s). In another example, the cancer stem cell(s) is characterised as (i) expressing EpCAM, (ii) is tumorigenic, (iii) is capable of self renewal, (iv) is capable of differentiating and (v) resistant to apoptosis by conventional therapy.

The cancer stem cell(s) may be alternatively described as isolated, enriched or purified from a source, such as a biological sample. In another example, the cancer stem cell(s) represent a population of cells enriched on the basis of EpCAM$^+$ expression. In another example, the population of cells comprises at least 10%, at least 20%, at least 30%, at least 40%, at least 50%, at least 60%, at least 70%, at least 80%, at least 90% or at least 95% cancer stem cells.

In one example, the EpCAM expressing cells and/or cancer stem cells are present in vivo. In another example, the EpCAM expressing cells and/or cancer stem cells are present in vitro. In a further example the EpCAM expressing cells and/or cancer stem cells are present in a biological sample obtained from a subject. In a further example, the biological sample is a biopsy sample.

In another example, the EpCAM expressing cells and/or cancer stem cells of the present disclosure may express one or more additional antigens including CD44, ABCG2, β33-catenin, CD133, ALDH, VLA-2, CD166, CD201, IGFR, and EGF1R.

In another example, the cancer stem cell according to the present disclosure is a brain cancer metastasis. In a further example, the metastasis is derived from a primary breast, liver, or colon cancer.

In another example, the aptamer conjugate specifically binds to the transferrin receptor (TfR). In another example, the aptamer conjugate is capable of passing through the blood, brain barrier. In another example, the transferrin receptor is transferrin receptor 1.

In another embodiment, the present disclosure also provides a detecting agent comprising an aptamer or aptamer conjugate as described herein coupled to a detectable label.

In another embodiment, the present disclosure also provides a diagnostic agent comprising the aptamer or aptamer conjugate as described herein coupled to a detectable label.

It would be appreciated by persons skilled in the art that the aptamer conjugates of the present invention avoid complications that may be associated with non-specific antibody binding and hence provide superior signal to noise ratio.

In one example, the detecting or diagnostic agent as described herein is used to detect for EpCAM expressing cells in vivo or in vitro.

In one example, the aptamer or aptamer conjugate of the present disclosure can be used to detect the presence of EpCAM expressing cells and/or cancer stem cells in a subject or in a biological sample obtained from a subject having a tumour or suspected of having a tumour.

In a further example, the aptamer or aptamer conjugate can be used to diagnose the presence of a brain tumour or brain metastasis in a subject or in a biological sample obtained from a subject having a tumour or suspected of having a tumour.

In a particular example, the detection or diagnosis is based on detecting EpCAM expressing cells.

Detection can be facilitated by coupling the aptamer or aptamer conjugate to a detectable label. Examples of detectable labels include various enzymes, prosthetic groups, fluorescent materials, luminescent materials, bioluminescent materials, electron dense labels, labels for MRI and radioactive materials.

The present disclosure also provides an aptamer or aptamer conjugate as described herein or the detecting agent as described herein for use in histological examination of biological samples. Methods for preparing histological preparations will be familiar to persons skilled in the art.

The present disclosure also provides an anticancer agent comprising an aptamer or aptamer conjugate as described herein coupled to a moiety. In one example, the anticancer agent as described herein is used to a treat brain tumour or cancer, and/or brain metastasis in a subject. Persons skilled in the art of the present disclosure will appreciate that the anticancer agent of the present disclosure can be used to treat cancers or tumours which have arisen de novo in the brain or which have developed from metastasis of a primary tumour or cancer originating outside of the brain. In one example, the subject is one which would benefit from treatment with the aptamer or aptamer conjugate of the present disclosure. In another example, the subject is one which has been diagnosed as having brain cancer or a brain tumour. Typically, a cancer will be recognised as an uncontrollable growth which is malignant and thus capable of generating secondary growths. A tumour may be malignant or benign. Benign tumours are characterised as growth limited to a certain part of the body. In another example, the subject is one having a solid tumour. With regard to their utility in the treatment of tumours, persons skilled in the art would appreciate that the aptamer or aptamer conjugate of the present disclosure may be used to deliver a moiety to such tumours which decreases tumour size and/or its ability to grow within the brain thus preventing or reducing the tumours ability to compromise brain function and/or integrity.

The aptamer or aptamer conjugate of the present disclosure can be coupled to a moiety and the aptamer used to direct the moiety to the site of a tumour which comprises, or is suspected of comprising EpCAM expressing cells (e.g. EpCAM expressing cancer stem cells). Examples of moieties include toxins, radionuclides or chemotherapeutic agents which can be used to kill EpCAM expressing cells, or imaging agents which can be used to locate and size tumours comprising EpCAM expressing cells. In a further example, the aptamer or aptamer conjugate is coupled with doxorubicin (dox). The doxorubicin is preferably inserted or intercalated into the stem region(s) of the aptamer or aptamer conjugate.

The anticancer agent comprising the aptamer or aptamer conjugate of the present disclosure can additionally include one or more effective ingredients. Effective ingredients may include one or more further anti-cancer agents.

The present disclosure also provides a method for isolating, purifying or enriching an EpCAM expressing cell(s) and/or cancer stem cell(s) from a biological sample obtained from a subject, the method comprising contacting the cell with an aptamer or aptamer conjugate of the present disclosure or the detecting agent of the present disclosure. In one example, the method is carried out in vitro.

Methods isolating, purifying or enriching EpCAM expressing cells are known to persons skilled in the art and are also described elsewhere herein.

The present disclosure also provides a method for identifying or detecting an EpCAM expressing cell(s) and/or cancer stem cell(s) in a subject or in a biological sample obtained from a subject having, or suspected of having brain cancer or a brain tumour and/or brain metastasis, comprising contacting the cell or sample with the aptamer or aptamer conjugate of the present disclosure, or the detecting agent of the present disclosure.

The present disclosure also provides a method of diagnosing brain cancer or a brain tumour and/or brain metastasis, comprising contacting EpCAM expressing cell(s) and/or cancer stem cell(s) in a subject or in a biological sample obtained from a subject with the aptamer conjugate of the present disclosure or the diagnostic agent of the present disclosure.

The present disclosure also provides a method for treating or preventing a brain cancer or tumour and/or brain metastasis in a subject, comprising providing the subject with an aptamer or aptamer conjugate as described herein or the anticancer agent as described herein. In one example, the cancer is any cancer in which EpCAM expressing cells and/or cancer stem cells are present or suspected of being present. The brain metastasis may be one which has originated from a primary cancer located elsewhere in the body and appearing in the brain months or years following treatment for the primary cancer.

EpCAM expressing cells can be found in brain tumours, including but not limited to astrocytoma, craniopharyngioma, esthesioneuroblastoma, neurofibroma, primitive neuroectodermal tumor (PNET). Additionally, EpCAM expressing cells are found in various tumours, including but not limited to skin tumours (e.g. basalioma, melanoma, Merkel cell carcinoma), thymoma, fibrosarcoma, mammary gland/breast tumours (e.g. apocrine carcinoma, cribriform carcinoma, ductal carcinoma, medullary carcinoma), endometrial tumours, ovarian tumours (e.g. endometriod carcinoma, endometrioid carcinoma, serous carcinoma), prostate carcinoma, kidney tumour, bladder tumour, lung tumour, colon and rectal tumours, (e.g. colon adenoma, colon adenocarcinoma), oesophageal tumour, hepatic tumours, pancreatic tumours, stomach tumours, and neuroendocrine tumours (e.g. carcinoid tumours, parathyroid adenoma, thyroid adenoma, thyroid follicular carcinoma, thyroid papillary carcinoma).

It will be appreciated that the methods of the present disclosure can be used to deliver whole body therapy to a subject. For example, depending upon the route of administration, the aptamer or aptamer conjugate can be used to target brain tumours/cancer or metastasis as well as tumours located in other parts of the body containing EpCAM expressing cells. In this way, the aptamer or aptamer conjugate can provide a whole body therapy approach to treatment.

In another example, the subject is one which has been diagnosed as having brain cancer or a brain tumour and/or brain metastasis. In another example, the subject is one having a solid tumour.

In another embodiment, the present disclosure also relates to the use of an aptamer or aptamer conjugate or anticancer agent as described herein in medicine.

The present disclosure also relates to the use of an aptamer or aptamer conjugate or anticancer agent as described herein for treating or preventing brain cancer, brain tumour and/or brain metastasis in a subject.

The present disclosure also relates to the an aptamer or aptamer conjugate or anticancer agent as described herein for use in treating or preventing brain cancer, brain tumour and/or brain metastasis in a subject.

The present disclosure also relates to the use of an aptamer or aptamer conjugate or anticancer agent as described herein in the manufacture of a medicament for treating or preventing brain cancer, a brain tumour and/or a brain metastasis in a subject.

In another embodiment, the present disclosure provides a delivery agent comprising an aptamer or aptamer conjugate as described herein coupled to an siRNA, ribozyme or DNAzyme.

In another embodiment, the present disclosure provides a composition comprising a therapeutically effective amount of an aptamer or aptamer conjugate, anticancer agent or delivery agent as described herein, together with a pharmaceutically acceptable carrier and/or excipient. In one example, the aptamer is delivered as a liposomal formulation.

In another embodiment, the present disclosure provides an aptamer or aptamer conjugate as described herein or the diagnostic agent as described herein for use in molecular imaging of brain cancer, brain tumour or brain metastasis.

The tumour penetrative ability of the aptamer or aptamer conjugate of the present invention provides a distinct advantage over antibodies for molecular imaging of tumours. For example, the aptamer or aptamer conjugate can be coupled to an agent which facilitates the detecting and imaging of cancer or tumours bearing EpCAM expressing cells. Examples of suitable agents include the detection labels as described herein.

The aptamer or aptamer conjugate, diagnostic agent, anticancer agent, delivery agent or pharmaceutical composition as described herein may be used alone or in combination with other treatment modalities. For example, the aptamer or aptamer conjugate, diagnostic agent, anticancer agent, delivery agent or pharmaceutical composition may be used in combination with chemotherapy and/or radiotherapy. While not wishing to be bound by theory, it is postulated that the chemotherapy or radiotherapeutic agents can be used to shrink tumours by primarily targeting rapidly dividing cells which are typically the progeny cells of the cancer stem cells. The diagnostic agent can be used to determine the effectiveness of any prior treatment modality to eliminate cancer stem cells by detecting the presence or absence of cancer stem cells in the tumor. The anticancer agent, delivery agent or pharmaceutical composition containing the aptamer or aptamer conjugate of the present disclosure can then be administered to the subject to specifically deplete EpCAM expressing cells. Accordingly, the anticancer agent, delivery agent or pharmaceutical composition containing the aptamer or aptamer conjugate can be used together with chemotherapy or radiotherapy or subsequent to chemotherapy or radiotherapy treatment. It is also contemplated that the aptamer or aptamer conjugate of the present disclosure can be combined with one or more additional aptamers which target an antigen present on a cancer stem cell.

Each example of the disclosure shall be taken to apply mutatis mutandis to a method for treating, preventing or ameliorating cancer in a subject.

Each example of the disclosure shall be taken to apply mutatis mutandis to molecular imaging of cancers or tumours.

DESCRIPTION OF THE DRAWINGS

FIGS. 5A-1 and A-2 shows determination of the equilibrium dissociation constants (KD) for the interaction of truncated loops against EpCAM positive cell lines, HT29 and HEY. Representative binding curves were determined at varying concentrations of EpCAM DNA aptamers (20-200 nM) using a cell density of 5×105 cells/mL. Data presented as median±SEM (n=3).

FIGS. 9-1 and 9-2 shows a determination of the $K_D$ of conjugate aptamers with TfR-positive (bEnd.3), EpCAM-positive (HEY) and -negative (MOLT4) cells. Top curve in each case corresponds to HEY cells and the lower curve to bEnd.3 cells. (A) Aptamer conjugate (Bi1); (B) Aptamer conjugate (Bi2); (C) Aptamer conjugate (Bi3). (D-F) Fluorescence histograms were obtained using concentrations 0 and 100 nM with MOLT4 cells. (D) Bi1; (E) Bi2; (F) Bi3. Data presented as median±SEM (n=3).

FIGS. 12-1 and 12-2 shows in vivo imaging of bi-functional aptamers. Mice were injected with 2 nanomoles of aptamer via tail vain injection. (A) Whole body fluorescent images captured during the 30 minute incubation period following administration. i) Neg control aptamer Bi1 (TENN) ii) Pos control aptamer Bi3 (TEPP) (B) 30 minutes following administration mice were sacrificed and the brain extracted. i) Neg ii) Pos (N=2).

FIG. 14A shows sequences and structures of the indicated aptamer constructs. TfR=mouse transferrin receptor aptamer, EpCAM=Epithelial cell adhesion molecule aptamer, Bi=bispecific aptamer.

KEY TO SEQUENCE LISTING

Figure 1:
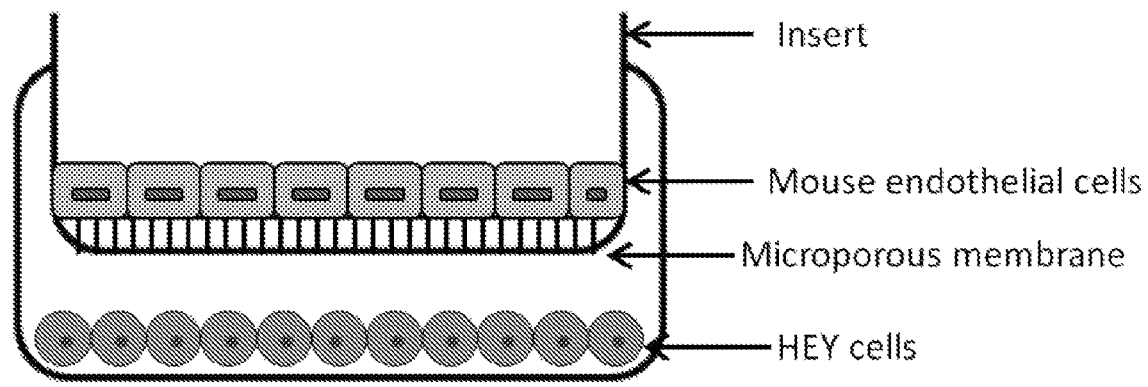
FIG. 1 shows a schematic of the in vitro model of the blood brain barrier used herein.

SEQ ID NO:1: consensus DNA sequence of the aptamer conjugate of the present disclosure.
SEQ ID NO:2: DNA sequence of an aptamer conjugate Bi2
SEQ ID NO:3: DNA sequence of an aptamer conjugate Bi3
SEQ ID NO:4: DNA sequence of aptamer TfR1
SEQ ID NO:5: DNA sequence of aptamer TfR2
SEQ ID NO:6 DNA sequence of aptamer TfR3
SEQ ID NO:7: DNA sequence of aptamer TfR4
SEQ ID NO:8: DNA sequence of aptamer conjugate Bi1
SEQ ID NO:9: DNA sequence of aptamer Ep7
SEQ ID NO:10: DNA sequence of aptamer conjugate (aptamer 6)
SEQ ID NO:11: DNA sequence of aptamer Ep8
SEQ ID NO:12: DNA sequence of aptamer Ep9
SEQ ID NO:13: DNA sequence of extended Ep7 aptamer (Ex Ep7)
SEQ ID NO:14: DNA sequence of scrambled extended Ep7 aptamer (scr ex ep7)
SEQ ID NO:15: DNA sequence of full length 64 mer TfR aptamer
SEQ ID NO: 16: DNA sequence of full length 48 mer EpCAM aptamer
SEQ ID NO:17: DNA sequence of TfR aptamer
SEQ ID NO:18: DNA sequence of TfR aptamer

DETAILED DESCRIPTION OF THE INVENTION

General Techniques and Selected Definitions

The term "and/or", e.g., "X and/or Y" shall be understood to mean either "X and Y" or "X or Y" and shall be taken to provide explicit support for both meanings or for either meaning.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example of the disclosure unless specifically stated otherwise. Those skilled in the art will appreciate that the disclosure is susceptible to variations and modifications other than those specifically described. It is to be understood that the disclosure includes all such variations and modifications. The disclosure also includes all of the steps, features, or compositions referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

The present disclosure is performed without undue experimentation using, unless otherwise indicated, conventional techniques of molecular biology, recombinant DNA technology, cell biology and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al, pp 35-81; Sproat et al, pp 83-115; and Wu et al, pp 135-151; 4. Nucleic Acid Hybridization: A Practical Approach (B. D. Flames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series, Sakakibara, D., Teichman, J., Lien, E. Land Fenichel, R. L. (1976). Biochem. Biophys. Res. Commun. 73 336-342; Merrifield, R. B. (1963). J. Am. Chem. Soc. 85, 2149-2154; Barany, G. and Merrifield, R. B. (1979) in The Peptides (Gross, E. and Meienhofer, J. eds.), vol. 2, pp. 1-284, Academic Press, New York. 12. Wunsch, E., ed. (1974) Synthese von Peptiden in Houben-Weyls Metoden der Organischen Chemie (Wier, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. J. Peptide Protein Res. 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word 'comprise', or variations such as 'comprises' or 'comprising', will be understood to imply the inclusion of a stated step or element or integer or group of steps or elements or integers but not the exclusion of any other step or element or integer or group of elements or integers.

The term 'consists of' or 'consisting of' shall be understood to mean that a method, process or composition of matter has the recited steps and/or components and no additional steps or components.

The term 'about', as used herein when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

The term 'apatmer' as used herein comprises a loop-like single-stranded region, and wherein regions adjacent to the both ends of the single-stranded region, respectively, preferably form a double-stranded stem region. An aptamer is known to comprise the so called "stem-loop structure" like this in many cases, and also known to bind specifically to a target substance mainly through the single-stranded loop structure region. The sizes of the regions which are adjacent to the both ends of the single-stranded region and which form the double-stranded region with each other are not restricted, and preferably 2 bp to 15 bp. The secondary structure of the aptamer can be determined easily by a conventional method using a computer. As a software for analysis of the secondary structure of the aptamer, well-known Mfold, for example, can be utilized, which software is freely available in the Mfold web server.

The double stranded stem region comprises paired bases. For example, the paired bases may be either A-T base pairs or C-G base pairs.

The term 'aptamer conjugate' as used herein refers to a construct which has bifunctional activity. In particular, it refers to a construct comprising at least one 'EpCAM binding portion' and at least one 'TfR binding portion'. In a particular example, the aptamer construct comprises one EpCAM binding portion and one TfR binding portion. In one example, the EpCAM binding portion is an aptamer and the TfR binding portion is an aptamer. The EpCAM binding portion (aptamer) and the TfR binding portion (aptamer) may be contiguous. Alternatively, the EpCAM binding portion (aptamer) and the TfR binding portion (aptamer) may be joined via a linker. Examples of suitable linkers include those which provide flexibility to the aptamer conjugate. In one example, the aptamer conjugate is a DNA aptamer. The term 'aptamer conjugate' also encompasses multimers.

By 'TfR binding portion' it is meant that part of the aptamer conjugate which is capable of binding to TfR and constitutes a stem region and a binding loop region. In one example, the TfR binding portion is an aptamer. The TfR binding portion is capable of binding to, or specifically binding to TfR.

By 'EpCAM binding portion' it is meant that part of the aptamer conjugate which is capable of binding to EpCAM and constitutes a stem region and a binding loop region. In one example the EpCAM binding portion is an aptamer. The EpCAM binding portion is capable of binding to, or specifically binding to EpCAM.

By 'EpCAM aptamer' it is meant an aptamer which is capable of binding to EpCAM and constitutes a stem region and a binding loop region.

As used herein the term 'binding affinity' and 'binding activity' are intended to refer to the tendency of the aptamer or the aptamer conjugate (and/or EpCAM and TfR binding portions thereof individually) to bind or not bind a target and describes the measure of the strength of the binding or affinity of the aptamer or aptamer conjugate and/or EpCAM and TfR binding portions thereof to bind the target. The energetics of said interactions are significant in 'binding activity' and 'binding affinity' because they define the necessary concentrations of interacting partners, the rates at which these partners are capable of associating, and the relative concentrations of bound and free molecules in a solution. The energetics are characterized herein through, among other ways, the determination of a dissociation constant, $K_D$. As is known in the art, a low dissociation constant indicates stronger binding and affinity of the molecules to each other. In one example, the dissociation constant is at least $10^{-6}$ M. In another example, the dissociation constant is at least $10^{-8}$ and $10^{-9}$ M. Binding affinity may also be expressed in terms of the equilibrium dissociation constant ($K_D$) which represents the ratio of the aptamer dissociation rate ($K_{off}$) to the aptamer association rate ($K_{on}$). The smaller the $K_D$ value, the greater the affinity of the aptamer for its target. $K_D$ values can be measured for example using either polarization-modulated oblique-incidence reflectivity difference (OI-RD) or Biacore.

As used herein, the term 'biological sample' refers to a cell or population of cells or a quantity of tissue or fluid from a subject. Most often, the sample has been removed from a subject, but the term 'biological sample' can also refer to cells or tissue analyzed in vivo, i.e. without removal from the subject. A 'biological sample' in the context of the present disclosure will contain tumour cells from the subject. Biological samples include, but are not limited to, tissue biopsies, or needle biopsies obtained from the brain tumour. Samples may be paraffin-embedded or frozen tissue. The sample can be obtained by removing a sample of cells from a subject, but can also be accomplished by using previously isolated cells (e.g. isolated by another person), or by performing the methods of the invention in vivo.

The term 'coupled to' as used herein is intended to encompass any construction whereby the aptamer conjugate is linked, attached, intercalated or joined to a detection agent, moiety, siRNA, ribozyme or DNAzyme as described herein. Methods for effecting coupling will be known to persons skilled in the art and include, but are not limited to, conjugation, linking via peptide or DNA linker or by direct chemical synthesis of the DNA and agent (e.g. DNAzyme) as a whole chain.

The term 'isolated' as used herein is intended to refer to the stem cell (e.g. cancer stem cell), isolatable or purified from other components. An isolated cell refers to a cell from the environment in which it may naturally occur. The isolated cell may be purified to any degree relative to its naturally-obtainable state.

The aptamer or aptamer conjugate of the present disclosure is preferably chemically synthesised using methods known in the art. Reference to the term 'isolated' in the context of the aptamer conjugate refers to an aptamer which is purified from other components which may be present during synthesis of the aptamer (e.g. SELEX method).

The term 'therapeutically effective amount' shall be taken to mean a sufficient quantity of aptamer or aptamer conjugate, anticancer agent, delivery agent or pharmaceutical composition according to the present disclosure to reduce or inhibit the number of EpCAM expressing cancer stem cells and/or one or more symptoms of cancer. The skilled artisan will be aware that such an amount will vary depending upon, for example, the particular subject and/or the type or severity or level of disease. The term is not be construed to limit the present disclosure to a specific quantity of aptamer or aptamer conjugate.

As used herein, the term 'treat' or 'treatment' or 'treating' shall be understood to mean administering a therapeutically effective amount of aptamer, aptamer conjugate, anticancer agent, delivery agent or pharmaceutical composition as disclosed herein and reducing or inhibiting at least one symptom of a clinical condition associated with or caused by cancer.

As used herein, the term 'prevent' or 'preventing' or 'prevention' shall be taken to mean administering a therapeutically effective amount of aptamer, aptamer conjugate, anticancer agent, delivery agent or pharmaceutical composition according to the present disclosure and stopping or hindering or delaying the development or progression of at least one symptom of cancer.

As used herein, the term 'specifically binds' shall be taken to mean that the aptamer or aptamer conjugate reacts or associates more frequently, more rapidly, with greater duration and/or with greater affinity with a particular cell (marker present on the cell) than it does with alternative cells (markers). For example, an aptamer or aptamer conjugate that specifically binds to a target protein binds that protein or an epitope or immunogenic fragment thereof with greater affinity, avidity, more readily, and/or with greater duration than it binds to unrelated protein and/or epitopes or immunogenic fragments thereof. Generally, but not necessarily, reference to binding means specific binding. The specificity of binding is defined in terms of the comparative dissociation constants (Kd) or equilibrium dissociation constants ($K_D$) of the aptamer conjugate for target as compared to the dissociation constant or equilibrium dissociation constant with respect to the aptamer or aptamer conjugate and other materials in the environment or unrelated molecules in general. Typically, the Kd or $K_D$ for the aptamer with respect to the target will be 2-fold, 5-fold, or 10-fold less than the Kd or $K_D$ with respect to the target and the unrelated material or accompanying material in the environment. Even more preferably, the Kd or $K_D$ will be 50-fold, 100-fold or 200-fold less.

The term 'EpCAM+' or 'EpCAM expressing cell(s)' as used herein may be used interchangeably. The term encompasses cell surface expression of the EpCAM antigen which can be detected by any suitable means. Reference to a cell being positive for a given marker means it may be either a low (lo or dim) or a high (bright, bri) expresser of that marker depending on the degree to which the marker is present on the cell surface, where the terms relate to intensity of fluorescence.

As used herein, the term 'subject' shall be taken to mean any subject, including a human or non-human subject. In one example, the subject is a human.

Aptamers

Aptamers are small oligonucleotides that are capable of binding to a specific target. They bind to the complementary ligand due to the interaction of the 3D structure with the target in a similar manner to antibodies, rather than by complementary base pairing. Aptamers have two unique domains: the non-binding stem region and the binding loop; and can be either DNA or RNA. DNA aptamers are more stable and inexpensive than RNA aptamers, but RNA aptamers have a more diverse range of functions (Shigdar S et al (2011) British Journal of Haematology 155(1):3-13). Aptamers are produced by a process known as Systematic Evolution of Ligands by Exponential Enrichment (SELEX).

Aptamers have a number of features that make them superior to antibodies for therapeutic applications. Firstly, they are smaller than their antibody protein counterparts (5-25 kDa vs 125 kDa), and thus are capable of penetrating deeper into a tissue and even through to the core of a tumour (Shigdar S et al, (2013) Cancer Letters 330(1):84-95). Also, unlike antibodies, aptamers have not been documented to produce an immune response. The production of aptamers is also a simpler process, as SELEX is an in vitro process, as opposed to antibodies, which are produced using the immune system of an animal. This ensures that aptamers can be manufactured against a wide range of epitopes and that there is limited batch-to-batch variation, both aspects which make them superior to antibodies.

However, there are a number of limitations associated with aptamers. Aptamers have a reduced circulatory half-life due to two factors. Firstly, being oligonucleotides, they are susceptible to nuclease degradation. Moreover, the smaller size of aptamers makes them susceptible to glomerular filtration, and so are easily passed out in the urine. Any post-SELEX modification to an aptamer has the potential to alter the binding affinity. Aptamers also have delivery problems, in part because of repulsion of the nucleic acid by the negatively-charged cell membrane.

Aptamers have the potential to be used for a multitude of purposes in a similar way to antibodies. An aptamer has already been approved by the FDA for clinical use in the treatment in macular degeneration (Rinaldi M et al, (2012) British Journal of Clinical Pharmacology 74(6):940-6), and several are currently undergoing clinical trials for a range of uses. Preclinical studies in vitro and in vivo have illustrated the therapeutic applications of aptamers in treating conditions from diabetes to HIV and prion diseases. These chemical antibodies, as they are sometimes known, are especially promising in the field of cancer research, as they can be used to target a specific marker on the surface of cancer cells to deliver a payload designed to elicit a cytotoxic effect. This approach has the potential to limit the systemic toxicity of a chemotherapeutic regime, by focusing the drugs towards the site of cancer. If such a technique could be applied clinically, it would limit patient side effects and enable the use of a higher drug dose. In addition, targeted treatments could be directed towards the tumorigenic CSCs, which would improve patient outcomes.

EpCAM

Cancer cells exhibit a different antigenic expression profile to normal cells, and this distinct pattern can become the focus of an anticancer treatment program. A number of cell surface markers are expressed at higher levels on cancer cells, and thus, aptamers can be generated that will bind to those cancer cells. The epithelial cell adhesion molecule (EpCAM) is a membrane glycoprotein that has been identified as a marker for solid tumours and CSCs due to its high levels (thousand-fold) of expression in comparison to normal epithelial cells (88-91). Interestingly, an immunohistochemical analysis of 108 samples of secondary tumours has found that only 4% lacked EpCAM expression. Furthermore, EpCAM is associated with poor patient prognosis, which is unsurprising, given it has been linked to cell proliferation and metastasis (93-95).

EpCAM is an ideal therapeutic target, because in normal cells it is expressed on the basolateral side of the epithelial membrane, whereas in cancer cells, EpCAM is heavily expressed on the apical surface. Antibody-based therapeutics have been able to exploit this characteristic of EpCAM expression, as normal cellular EpCAM is less prominent and less exposed, meaning healthy cells are not as susceptible to antibody binding. Hence, side effects are limited and drug action is directed towards the problem cells.

Clinical studies involving anti-EpCAM therapeutic antibodies for the treatment of cancer have observed the development of acute pancreatitis in patients. However, this side effect was only seen in antibodies with a high affinity. This suggests that aptamer-based targeting of EpCAM should use aptamers with a moderate binding affinity in order to limit side effects. EpCAM is a useful target for aptamer-based cancer therapy, particularly for brain tumours, as normal brain tissue is negative for EpCAM (Amann M et al, (2008) Cancer Research 68(1):143-51). Hence, if the BBB could be bypassed, EpCAM would be an ideal target for the treatment of brain metastases and/or brain cancer.

Aptamer-Doxorubicin Conjugates

In order to kill cancer cells, an aptamer must be conjugated to something that will provoke a cytotoxic effect. One option is to conjugate the aptamer with a chemotherapeutic drug to directly kill the cancer cells. Doxorubicin (dox) is a drug which has been conjugated with aptamers. Due to the anthracycline structure of dox, it can readily insert (reaching equilibrium within ten seconds) into the stem region of an aptamer, between guanine-cytosine (GC) pairs, with minimal alteration in the binding affinity. This reflects the mechanism of dox toxicity, as it intercalates into the DNA of a cell, inducing apoptosis. Aptamers can be engineered so as to have an extended stem region with a high GC content, allowing increased intercalation with dox. Aptamer-dox conjugates have been produced which are internalised into cells via RME and illicit a cytotoxic effect comparable to free dox and display six-times greater toxicity against cancer cells than normal cells. An advantage of this system is the pH-mediated drug release. These conjugates are stable at plasma (7.4) and brain (6.6-7.2) pH, but dissociate upon internalisation into the more acidic environment of the endosome.

Selection of Aptamers for a Given Target

Aptamers that bind to virtually any particular target can be selected by using an iterative process called SELEX™ (Systemic Evolution of Ligands by EXponential Enrichment). The process is described in, for example U.S. Pat. Nos. 5,270,163 and 5,475,096. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

The SELEX™ process relies, as a starting point, upon a large library or pool of single stranded oligonucleotides comprising randomised sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs, hybridization sites for PCR primers, promoter sequences for RNA/DNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomised sequence portion as well as fixed sequences necessary for efficient amplification. Typically, the oligonucleotides of the starting pool contain fixed 5' and 3' terminal sequences which flank an internal region of 30-50 random nucleotides. The randomised nucleotides can be produced in a number of ways including chemical synthesis and size selection from randomly cleaved cellular nucleic acids. Sequence variation in the test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs (see for example U.S. Pat. Nos. 5,958,691, 5,660,985 and WO 92/07065). Random oligonucleotides can be synthesized from phosphodiester-linked nucleotides using solid phase oligonucleotide synthesis techniques well known in the art. See, for example, Froehler et al., (1986). Nucl. Acid Res. 14:5399-5467 and Froehler et al (1986) Tet. Lett. 27:5575-5578. Random oligonucleotides can also be synthesized using solution phase methods such as triester synthesis methods. See, e.g., Sood et al (1977). Nucl. Acid Res. 4:2557 and Hirose et al (1978). Tet. Lett., 28:2449. Typical syntheses carried out on automated DNA synthesis equipment yield $10^{14}$-$10^{16}$ individual molecules, a number sufficient for most SELEX™ experiments.

The starting library of oligonucleotides may be generated by automated chemical synthesis on a DNA synthesiser. Partially random sequences can be created by adding the four nucleotides in different molar ratios at each addition step.

The starting library of oligonucleotides may be either RNA or DNA. In those instances where an RNA library is to be used as the starting library it is typically generated by transcribing a DNA library in vitro using T7 RNA polymerase or modified T7 RNA polymerases and purified. The RNA or DNA library is then mixed with the target under conditions favourable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Cycles of selection and amplification are repeated until a desired goal is achieved. Generally this is until no significant improvement in binding strength is achieved on repetition of the cycle. Typically, nucleic acid aptamer molecules are selected in a 5 to 20 cycle procedure. A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photo reactive groups capable of binding and/or photo-crosslinking to and/or photoinactivating a target molecule. U.S. Pat. Nos. 5,567,588 and 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; (e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for SELEX™, cycles of selection and amplification are repeated as necessary until a desired goal is achieved.

In a representative example, an aptamer is synthesized on a solid support column, using conventional techniques such as those described by Beaucage et al. (1981) Tetrahedr. Letters 22:1859-1862 and Sinha et al., (1984) Nucleosides and Nucleotides 3:157-30 171. Alternately, if large scale synthesis is used, the aptamer can be made by scale-up of the solid support method or the aptamer can be made by using solution phase techniques, particularly if the desired end-product is a relatively short oligonucleotide. A starting material for the synthesis process can be a 5'-non-tritylated RNA oligoribo-nucleotide or analog of the desired primary structure, which preferably can have protected bases, and which is preferably bound to a solid-support. Any conventionally used protecting groups can be used. Typically N 6-benzoyl is used for adenine, N 4-benzoyl for cytosine, N 2-isobutyryl for guanine and N 2-benzoyl for 2-amino purine. Other useful protecting groups include phenoxy-acetyl (PAC) and t-butoxyacetyl (TAC). Conveniently, the more base labile protection groups should be used for the synthesis of the aptamer; those of ordinary skill in the art know these groups. Such groups can help to prevent hydrolysis of the generated tri- or diphosphates, which are generally quite stable under basic conditions, but could be subject to some hydrolysis. Other envisioned modifications are disclosed in U.S. Pat. No. 6,011,020, and include but are not limited to the incorporation of bioavailability enhancing molecules such as PEG or cholesterol via a covalent linkage.

In addition, nucleoside analogs such as 2'-deoxy, 2'-halo, 2'-amino (not substituted or mono- or disubstituted), 2'-mono, di- or trihalomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$ alkyl groups, abasic linkers, 3'-deoxy-adenosine as well as other available "chain terminator" or "non-extendible" analogs (at the 3'-end of the aptamer), and the like can be incorporated during the synthesis. Further, various labels such as $^{32}P$ or $^{33}P$ and the like can likewise be incorporated during the synthesis, resulting in novel analogs produced by this process. Other envisioned modifications are disclosed in U.S. Pat. No. 6,011,020, and include but are not limited to the incorporation of 3' caps, such an inverted DT cap, or an inverted abasic cap, or combination thereof.

Binding Affinity of Aptamers

The binding affinity describes the measure of the strength of the binding or affinity of molecules to each other. Binding affinity of the aptamer herein with respect to targets and other molecules is defined in terms of dissociation constant (Kd) or equilibrium dissociation constant ($K_D$). The dissociation constant can be determined by methods known in the art and can be computed even for complex mixtures by methods such as those, for example, set forth in Caceci, M., et al., Byte (1984) 9:340-362.

Examples of measuring dissociation constants are described for example in U.S. Pat. No. 7,602,495 which describes surface Plasmon resonance analysis, U.S. Pat. Nos. 6,562,627, 6,562,627, and US 2012/00445849. In another example, the dissociation constant is established using a double-filter nitrocellulose filter binding assay such as that disclosed by Wong and Lohman, (1993). Proc. Natl. Acad. Sci. USA 90, 5428-5432.

It has been observed, however, that for some small oligonucleotides, direct determination of dissociation constant is difficult, and can lead to misleadingly high results. Under these circumstances, a competitive binding assay for the target molecule or other candidate substance can be conducted with respect to substances known to bind the target or candidate. The value of the concentration at which 50% inhibition occurs (K) is, under ideal conditions, equivalent to $K_D$. A K value can also be used to confirm that an aptamer of the present invention binds a target.

Improving Aptamer Stability

One potential problem encountered in the use of nucleic acids as therapeutics in that oligonucleotides in their phosphodiester form may be quickly degraded in body fluids by intracellular and extracellular enzymes such as endonucleases and exonucleases before the desired effect is manifest. The present disclosure also includes analogs as described herein and/or additional modifications designed to improve one or more characteristics of the aptamer such as protection from nuclease digestion.

Oligonucleotide modifications contemplated in the present disclosure include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole.

Modifications to generate oligonucleotides which are resistant to nucleases can also include one or more substitute internucleotide linkages, altered sugars, altered bases, or combinations thereof. Such modifications include 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, and unusual base-pairing combinations such as the isobases isocytidine and isoguanosine; 3' and 5' modifications such as capping; conjugation to a high molecular weight, non-immunogenic compound; conjugation to a lipophilic compound; and phosphate backbone modification. Preferably, the aptamer comprises a 3' inverted thymidine.

In one example, the non-immunogenic, high molecular weight compound conjugated to the aptamer of the present disclosure is polyalkylene glycol, preferably polyethylene glycol. In one example, the backbone modification comprises incorporation of one or more phosphorothioates into the phosphate backbone. In another example, the aptamer of the present disclosure comprises the incorporation of fewer than 10, fewer than 6, or fewer than 3 phosphorothioates in the phosphate backbone.

The Blood Brain Barrier

Treatment of brain cancers or tumours is complicated by the presence of the blood brain barrier (BBB) which isolates the brain microenvironments from the systemic circulation by strictly regulating the passage of molecules. As such chemotherapeutic drugs are scarcely able to enter the brain, although they can still do damage elsewhere in the body. The BBB consists of a monolayer of cerebrovascular endothelial cells that line the brain microvessels. These are tightly packed together by a variety of cell-cell adhesion molecules, associated with both the membrane, such as claudins, and the cytoplasm. The latter type, which includes zona occuldens, serve to link the cytoskeletons of adjacent cells together. Other cell types are also involved in regulating the properties of the BBB, including astrocytes and pericytes. However, the most important component is the endothelial monolayer, which forms the physical barrier via tight junctions. The BBB is characterised by the unique expression of molecular transporters and specialist enzymes that regulate the passage of substances into and out of the brain parenchyma.

Metastasis

Tumours shed millions of cells each day, yet few of these go on the seed tumours at other sites in the body. The reasons for this failure rate is due to two factors; the fact that the cells shed are mostly dead, and the harsh environment cells encounter in circulation. Successful metastasis involves two separate processes, the release of a cell from the tumour mass and the intravasation into the circulatory or lymphatic systems, and the extravasation from the blood and the colonisation in another tissue. These are both thought to occur via phenotypic switches, that allow a cell to firstly migrate, and then to colonise other tissues. This morphological change involves the inter-conversion between epithelial and mesenchymal traits.

Like anti-cancer drugs, metastatic cells struggle to enter the brain parenchyma due to the presence of the BBB. As such it is unsurprising that extravasation into the brain is measurably longer than into other organs. While there remain many uncertainties regarding the exact mechanism of brain metastasis, it seems that cancer cells pass through the BBB via the paracellular route, by degrading the endothelial tight junctions and navigating between the endothelial cells.

Research by Kienast and co-workers (2010) Nat Med 16(1):116-22 has been critical in elucidating the processes by which cancer cells enter the brain. Using multi-photon laser scanning microscopy they identified four distinct stages. Firstly, a cancer cell is arrested in the brain capillaries and remains so for potentially days. Importantly, this occurs due to limitations in the microvessel diameter rather than any adhesive properties of the cell. While in this static state, the cell undergoes morphological changes, which place mechanical pressure on the BBB. The second step is the extravasation into the brain tissue, which involves enzymes, such as matrix metalloproteases that overcome the natural BBB defence against such enzymes and disrupt the endothelial tight junctions. Next it is important for a cancer cell to adhere to the abluminal side of the BBB in a similar manner to pericytes. From here, cells proliferate by co-opting existing vasculature or by promoting the formation of neovasculature via angiogenesis.

Utility of the Aptamers

The aptamer and aptamer conjugates of the present disclosure can be used as affinity ligands to separate and purify target molecules (e.g. EpCAM bearing cells), as probes to trace, monitor, detect and quantitate target molecules (e.g. EpCAM bearing cells), or to block, allow, activate or catalyse reactions that are physiologically relevant to achieve therapeutic effect. They can act as pharmaceutical agent, bind to a specific target and direct specific molecules to a desired site.

The aptamer and aptamer conjugates of the present disclosure can be used in in vitro processes, for example affinity purification mixtures to purify target molecules (e.g. EpCAM bearing cells). The aptamers are ideal for chromatographic separations of target molecules (e.g. EpCAM bearing cells) from contaminants and for purifying target molecules from cell cultures or cell extracts.

In one example, the aptamer and aptamer conjugates of the present disclosure can be used as capture agents to bind or immobilise a target (e.g. EpCAM bearing cells) to a solid support. The solid support can be comprised of substrates having the structure and composition commonly associated with filters, wafers, wafer chips, membranes and thin films.

However, it is contemplated that the solid support may be comprised of substrates including, but not limited to resins, affinity resins, magnetic or polymer beads, or any diagnostic detection reagent, to capture or immobilise reagents for diagnostic, detection or quantitative studies.

The solid supports may comprise any material depending of the desired use, including but not limited to glass, metal surfaces and materials such as steel, ceramic or polymeric materials such as polyethylene, polypropylene, polyamide, and polyvinylidenefluoride etc or combinations thereof.

Isolation and Purification of EpCAM Expressing Cancer Stem Cells

Cancer stem cells may be derived from any cancer comprising tumourigenic stem cells, i.e. cells having an ability to proliferate extensively or indefinitely, and which give rise to the majority of cancer cells. Within an established tumour, most cells have lost the ability to proliferate extensively and form new tumours, and a small subset of cancer stem cells proliferate to thereby regenerate the cancer stem cells as well as give rise to tumour cells lacking tumorigenic potential. Cancer stem cells may divide asymmetrically and symmetrically and may show variable rates of proliferation. Cancer stem cell may include transit amplifying cells or progenitor cells that have reacquired stem cell properties.

Representative cancers from which the EpCAM expressing cancer stem cells may be isolated include brain tumours or brain metastasis derived from a primary cancer including, but not limited to fibrosarcoma, myxosarcoma, liposarcoma, chondrosarcoma, osteogenic sarcoma, chordoma, angiosarcoma, endotheliosarcoma, lymphangiosarcoma, synovioma, lymphagioendotheliosarcoma, mesothelioma, Ewing's tumour, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma.

Additionally, the brain metastasis may be derived from a primary tumour or cancer selected from hematopoietic malignancies, such as B cell lymphomas and leukemias, including low grade/follicular non-Hodgkin's lymphoma (NHL), small lymphocytic (SL) NHL, intermediate grade/follicular NHL, intermediate grade diffuse NHL, high grade immunoblastic NHL, high grade small non-cleaved cell NHL, bulky disease NHL and Waldenstrom's Macroglobulinemia, chronic leukocytic leukemia, acute myelogenous leukemia, chronic myelogenous leukemia, lymphoblastic leukemia, lymphocytic leukemia, monocytic leukemia, myelogenous leukemia and promyelocytic leukemia.

Cancer stem cells bearing EpCAM may be selected using the aptamer or aptamer conjugates as described herein. For example, aptamers which are coupled to fluorescent dyes can be used for the positive selection of cancer stem cells. EpCAM is also known to be expressed in some normal cells. However, EpCAM expression is thought to be upregulated in cancer stem cells. Cancer stem cell markers are typically expressed at a level that is at least about 5-fold greater than differentiated cells of the same origin or non-tumorigenic cells, for example, at least about 10-fold greater, or at least about 15-fold greater, or at least about 20-fold greater, or at least about 50-fold greater, or at least about 100-fold greater. The selection process may also include negative selection markers which can be used for the elimination of those cancer cells in the population that are not cancer stem cells.

It will be understood that in performing the present disclosure, separation of cells bearing EpCAM can be effected by a number of different methods. For example, the aptamer or aptamer conjugate of the present disclosure may be attached to a solid support to allow for a crude separation. Various techniques of different efficacy may be employed depending upon efficiency of separation, associated cytotoxicity, ease and speed of performance and necessity for sophisticated equipment and/or technical skill. Procedures for isolation or purification may include, but are not limited to, magnetic separation using aptamer-coated magnetic beads, affinity chromatography and "panning" with aptamer attached to a solid matrix. Techniques providing accurate isolation or purification include but are not limited to FACS. Methods for preparing FACS will be apparent to the skilled artisan.

Enrichment of of EpCAM Expressing Cells

In one example, the EpCAM expressing cells are enriched from a biological sample obtained from a subject. Typically the subject will be one which has a brain tumour or is suspected of having a brain tumour or brain metastasis containing cancer stem cells. The term 'enriched' or 'enrichment' or variations thereof are used herein to describe a population of cells in which the proportion of one particular cell type (i.e. cancer stem cells) is increased when compared with an untreated population of the cells (e.g. cells in the sample).

In one example, a population enriched for cancer stem cells comprises at least about 0.1%, or 0.5% or 1% or 2% or 5% or 10% or 15% or 20% or 25% or 30% or 50% or 75% EpCAM bearing cancer stem cells. In this regard, the term 'enriched cell population comprising cancer stem cells' will be taken to provide explicit support for the term 'population of cells comprising X % cancer stem cells', wherein X % is a percentage as recited herein. In one example, the population of cells is enriched from a cell preparation comprising EpCAM+ cells in a selectable form. In this regard, the term 'selectable form' will be understood to mean that the cells express a marker (e.g. a cell surface marker) permitting selection of EpCAM bearing cells.

Diagnosis of Cancer Using Aptamer Conjugates

The aptamer and aptamer conjugates of the present disclosure can be used in vitro for diagnostic purposes to determine the presence of cancer stem cells in malignant tissue. The method involves examining a biological sample for the presence of EpCAM+ cancer stem cells. For example, the biological sample can be contacted with a labelled aptamer of the present disclosure and the ability of the aptamer to specifically bind to the cells in the sample is determined. Binding by the aptamer indicates the presence of an EpCAM bearing cell. In one example the EpCAM bearing cell is a cancer stem cell.

The aptamer conjugate of the present disclosure can also be used to localise a EpCAM+ tumour in vivo by administering to a subject an isolated aptamer of the present disclosure which is labelled with a reporter group which gives a detectable signal. Bound aptamers can then be detected using flow cytometry, microscopy, external scintigraphy, emission tomography, optical imaging or radionuclear scanning. The method can be used to stage a cancer in a subject with respect to the extent of the disease and to monitor changes in response to therapy.

Detection of cancer stem cells can be facilitated by coupling the aptamer or aptamer conjugate to a detectable label. Examples of detectable labels include various enzymes, prosthetic groups, fluorescent materials, luminescent materials, bioluminescent materials, electron dense labels, labels for MRI, and radioactive materials. Examples of suitable enzymes include horseradish peroxidise, alkaline phosphatise, β-galactosidase, or acetylcholinesterase. Examples of suitable prosthetic group complexes include streptavidin/biotin and avidin/biotin. Examples of suitable fluorescent materials include umbellifone, fluorescein isothiocyanate, rhodamine, dischlorotriazinylamine fluorescein, dansyl chloride or phycoerythrin. An example of a luminescent material includes luminol. Examples of bioluminescent materials include luciferase, luciferin, and aequorin, and examples of suitable radioactive material include $^{125}I$, $^{131}I$, $^{35}S$, $^{18}F$, $^{64}Cu$, $^{94m}Tc$, $^{124}I$, $^{11}C$, $^{13}N$, $^{15}O$, $^{68}Ga$, $^{86}Y$, $^{82}Rb$ or $^{3}H$.

Labelling at the 3' end of the aptamer can be achieved, for example by templated extension using Klenow polymerase, by T4 RNA/DNA ligase-mediated ligation and by terminal deoxynucleotidyl transferase. Labelling at the 5' end can be achieved by the supplementation of the in vitro transcription mix with an excess of GTP-13-S, the thiol of which can then be used to attach biotin. In addition, direct chemical conjugation of a suitable group(s) to either 5'- or 3'-end can be used to label the aptamers.

Anticancer Agent of the Present Disclosure

The aptamer or aptamer conjugates of the present disclosure can be further conjugated to a moiety and used to direct the moiety to EpCAM+ cells, preferably cancer stem cells. Examples of moieties include toxins, radionuclides, or chemotherapeutic agents which can be used to kill cancer stem cells.

The aptamer or aptamer conjugate can be fused to the moiety, e.g. the toxin, either by virtue of the moiety and aptamer being chemically synthesised, or by means of conjugation, e.g. a nonpeptide covalent bond, e.g. a non-amide bond, which is used to join separately produced aptamer and the moiety. Alternatively, the aptamer and moiety may be joined by virtue of a suitable linker peptide.

Useful toxin molecules include peptide toxins, which are significantly cytotoxic when present intracellularly. Examples of toxins include cytotoxins, metabolic disrupters (inhibitors and activators) that disrupt enzymatic activity and thereby kill cancer stem cells, and radioactive molecules that kill all cells within a defined radius of the effector portion. A metabolic disrupter is a molecule, e.g. an enzyme or a cytokine that changes the metabolism of a cell such that is normal function is altered. Broadly, the term toxin includes any effector that causes death to a tumour cell.

Many peptide toxins have a generalised eukaryotic receptor binding domain; in these instances the toxin must be modified to prevent killing cells not bearing EpCAM (e.g. to prevent killing cells not bearing EpCAM but having a receptor for the unmodified toxin). Such modifications must be made in a manner that preserves the cytotoxic function of the molecule. Potentially useful toxins include, but are not limited to diphtheria toxin, cholera toxin, ricin, 0-Shiga-like toxin (SLT-I, SLT-II, SLT-1I v), LT toxin, C3 toxin, Shiga toxin pertussis toxin, tetanus toxin, Pseudomonas exotoxin, alorin, saponin, modeccin and gelanin. Other toxins include tumor necrosis actor alpha (TNF-alpha) and lymphotoxin (LT). Another toxin which has antitumor activity is calicheamicin gamma 1, a diyne-ene containing antitumor antibiotic with considerable potency against tumors (Zein N et al (1988). Science 240:1198-201).

As an example, diphtheria toxin (which sequence is known) can be conjugated to the aptamer conjugates of the present disclosure. The natural diphtheria toxin molecule is secreted by Corynebacterium diptheriae consist of several functional domains that can be characterised, starting at the amino terminal end of the molecule, as enzymatically-active fragment A (AA 1-193) and fragment B (AA 194-535) which includes a translocation domain and a generalised cell binding domain (AA 475-535).

The aptamer and the toxin moiety can be linked in any of several ways which will be known to persons skilled in the art. For example, a method of conjugating an aptamer to a toxin (gelonin) is described in Chu T C et al. (2006) Cancer Res 6(12)5989-5992. The moiety can also be a modulator of the immune system that either activates or inhibits the body's immune system at the local level. For example, cytokines e.g. lymphokines such as IL-2, delivered to a tumour can cause the proliferation of cytotoxic T-lymphocytes or natural killer cells in the vicinity of the tumour.

The moiety or reporter group can also be a radioactive molecule, e.g. a radionucleotide, or a so-called sensitizer, e.g. a precursor molecule that becomes radioactive under specific conditions, e.g. boron when exposed to a bean of low-energy neutrons, in the so-called "boron neutron capture therapy" (BNCT) as described in Barth et al. (1990). Scientific American October 1990:100-107. Compounds with such radioactive effector portions can be used both to inhibit proliferation of cancer stem cells in the tumour and to label the cancer stem cells for imaging purposes.

Radionucleotides are single atom radioactive molecules that can emit either α, β, or γ particles. Alpha particle emitters are preferred to β, or γ particle emitters, because they release far higher energy emissions over a shorter distance, and are therefore efficient without significantly penetrating, and harming, normal tissues. Suitable particle emitting radionuclides include $^{211}At$, $^{212}Pb$, and $^{212}Bi$.

The radioactive molecule must be tightly linked to the aptamer either directly or by a bifunctional chelate. This chelate must not allow elution and thus premature release of the radioactive molecule in vivo. Waldmann, Science, 252: 1657-62 (1991). As an example, to adapt BNCT to the present invention, a stable isotope of boron, e.g., boron 10, can be selected as the antitumor moiety or effector portion of the compound. The boron will be delivered to and concentrates in or on the tumour cells by the specific binding of the aptamer to the cancer stem cell. After a time that allows a sufficient amount of the boron to accumulate, the tumour can be imaged and irradiated with a beam of low-energy neutrons, having an energy of about 0.025 eV. While this neutron irradiation, by itself, causes little damage to either the healthy tissue surrounding the tumour, or the tumour itself, boron 10 (e.g., on the surface of a tumour cell) will capture the neutrons, thereby forming an unstable isotope, boron 11. Boron 11 instantly fissions yielding lithium 7 nuclei and energetic a particles, about 2.79 million eV. These heavy particles are a highly lethal, but very localized, form of radiation, because particles have a path length of only about one cell diameter (10 microns).

Delivery Agent of the Present Disclosure

The aptamer conjugates of the present disclosure can be used for siRNA, ribozyme, or DNAzyme delivery into cells. Examples of suitable siRNA, ribozyme or DNAzyme will depend upon the circumstances. Examples of siRNAs, ribozymes, or DNAzymes that are suitable for use according to the present disclosure include those which target ATP binding cassette membrane transporters, sternness genes (Bmi-1, Notch 1, Sox 2, Oct-4, Nanog, β-catenin, Smo, nestin, ABCG2, Wnt2 and SCF, etc), GAPDH (glyceraldehyde 3-phosphate dehydrogenase), and survivin.

By way of example, this has been demonstrated in the prior art using an anti-PSMA aptamer. Based on the knowledge that PSMA is internalised via clathrin-coated pits to endosome, it was postulated that the anti-PSMA aptamer would carry the attached siRNA to the cells that express PSMA, and the aptamer-siRNA bound to the PSMA protein would gain access to the cell via internalisation. Next, the siRNA portion would undergo processing by the Dicer complex and feed into the RNA-Induced Silencing Complex (RISC)-mediated gene silencing pathway. Three groups have utilised different strategies to accomplish this. Chu et al (2006) Nucleic Acids Res 34, e73 describes a biotin-streptavidin bridge mediated conjugation method to assemble the anti-PSMA aptamer and the siRNA. McNamara et al. (2006) Nat Biotechnol 24, 1005-1015 used a "RNA-only" aptamer-siRNA chimera approach to link the aptamer and the siRNA. In a subsequent study by Wullner et al (2008). Curr. Cancer Drug Targets 8:554-565, the authors used the anti-PSMA aptamer to deliver Eukaryotic Elongation Factor 2 (EEF2) siRNA to PSMA-positive prostate cancer cells, Bivalent PSMA aptamers were used for this purpose. The authors demonstrated that, compared to the monovlaent anti-PSMA-siRNA chimera, the gene knockdown potency of the bivalent aptamer-construct was superior. The aptamer conjugates of the present disclosure can also be used to deliver cargo into EpCAM+cancer stem cells in a variety of solid tumours. Gelonin is a ribosomal toxin that can inhibit the process of protein synthesis and is cytotoxic. However, it is membrane impermeable and needs an usher for its cellular entry. Thus, the aptamer conjugates of the present disclosure can be utilised to deliver membrane impermeable toxic payload to cancer stem cells. Tumour resistance to cytotoxic chemotherapeutic agents is due in part to insufficient delivery to and uptake, and more importantly, efflux by cancer cells. Biodegradable nanoparticle (NP) derived from poly(D,L-lactic-co-glycolic acid) PLGA were used to address this problem as described in Dhar et al (2008) Proc. Natl. Acad. Sci. USA 105:17356-17361. Briefly, cisplatin was converted to its pro-drug, Pt(IV) compound, by introducing two alkyl chains. This increased the hydrophobicity of the compound and eased the process of its packaging within the hydrophobic core of the NP. Polyethylene glycol (PEG) was used as a copolymer during the nanoprecipitation step to synthesise the PLGA-PEG nanoparticle. The PLGA-PEG-NP surface was decorated with a PSMA (prostate specific membrane antigen) aptamer. The NP underwent endocytosis when incubated with LNCaP cells, and the alkylated pro-drug was converted to cisplatin by the cytosolic reduction process.

The present disclosure also extends to the use of the aptamer or aptamer conjugates as simultaneous drug delivery and imaging agents for brain tumours or brain metastases. This can be achieved by conjugating the aptamer to the surface of a fluorescent quantum dot (QD). Next, the QD-aptamer conjugate is incubated with Dox to form the QD-aptamer-Dox nanoparticle. Both Dox and QD are fluorescent molecules. However, due to their proximity in the QD-aptamer-Dox nanoparticle, they quench each other's fluorescence by a bi-fluorescence resonance energy transfer (FRET) mechanism. Thus, the QD-aptamer-Dox nanoparticle is non-fluorescent. However, internalisation of the QD-aptamer-Dox nanoparticle via PSMA-mediated endocytosis in cancer cells causes the release of Dox from the QD-aptamer-Dox nanoparticles, that results in the recovery of fluorescence by both Dox and QD.

Pharmaceutical Compositions

In one example of the present disclosure the aptamer, aptamer conjugate, anticancer agent or drug delivery agent according to the present disclosure is administered in the form of a composition comprising a pharmaceutically acceptable carrier and/or excipient. The choice of excipient or other elements of the composition can be adapted in accordance with the route and device used for administration.

The terms 'carrier' and 'excipient' refer to compositions of matter that are conventionally used in the art to facilitate the storage, administration, and/or the biological activity of an active compound/aptamer (see, e.g., Remington's Pharmaceutical Sciences, 16th Ed., Mac Publishing Company (1980). A carrier may also reduce any undesirable side effects of the active compound/aptamer. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g. water, saline, aqueous dextrose, lactose, Ringer's solution a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

Other general additives such as anti-oxidative agent, buffer solution, bacteriostatic agent etc can be added. In order to prepare injectable solutions, pills, capsules, granules, or tablets, diluents, dispersing agents, surfactants, binders and lubricants can be additionally added.

The anticancer agent or drug delivery agent containing the aptamer of the present disclosure can be administered to the subject for delivery to the brain according to methods known in the art. Administration may be by parental means (for example, intravenous, hypodermic, local or peritoneal injection). Alternatively administration may be intranasal. In some embodiments, the aptamer or aptamer conjugate is provided in the form of a nanoparticle or liposome. For example, nanoparticles can be functionalised with an aptamer or apatmer conjugate of the present disclosure for target delivery of drugs.

The effective dosage of the anticancer agent can be determined according to weight, age, gender, health condition, diet, administration frequency, administration method, excretion and severity of a disease. In one example, the anticancer agent or drug delivery agent contains the aptamer conjugate by 10-95 weight %. In another example, the anticancer agent or drug delivery agent contains the aptamer conjugate by 25-75 weight %.

The administration frequency may be one to several times a day. In one example, the effective intracellular content of the aptamer is approximately 1 nM to 1000 nM. In another example, the effective intracellular content of the aptamer is preferably 100 nM to 500 nM. However, the dosage of the aptamer could be under or more than the above range.

Transferrin Receptor

The transferrin receptor (TfR; CD71) is a transmembrane glycoprotein consisting of two 90 kDa subunits. A disulphide bridge links these subunits and each subunit can bind one transferrin (Tf) molecule. The TfR is expressed mainly on hepatocytes, erythrocytes, intestinal cells, monocytes, as well as on endothelial cells of the blood brain barrier (BBB). Furthermore, in the brain the TfR is expressed on choroid plexus epithelial cells and neurons. The TfR mediates the internalisation of iron-saturated transferrin by receptor mediated endocytosis. Studies have shown that the affinity of transferrin for its receptor depends on pH and iron loading.

Upon binding of the transferrin ligand to the receptor, the receptor-ligand complex is endocytosed via clathrin-coated vesicles.

Combinations of Aptamers

The isolated aptamer molecule(s) of the present disclosure can be used alone or in combination with one or more additional aptamers according to any method disclosed herein. in one example, the aptamer conjugate(s) of the present disclosure can be combined with an aptamer that facilitates the detection, purification or enrichment of cancer stem cells.

Kits

The present disclosure also provides diagnostic kits for carrying out the methods disclosed herein. In one example, the diagnostic kit includes the the diagnostic agent as described herein for detecting EpCAM expressing cells (e.g. cancer stem cells).

The kit may also include ancilliary agents such as buffering agents and stabilising agents. The diagnostic kit may further include agents for reducing background interference, control reagents and an apparatus for conducting a test. Instructions on how to use the diagnostic kit are generally also included.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Methods

Cell Culture

Cell lines (Table 1) were purchased from the American Type Culture Collection (ATCC) and were maintained in Dulbecco's Modified Eagle's Medium (DMEM; Invitrogen), supplemented with 10% foetal calf serum (FCS) at 37° C. in a 5% $CO_2$ atmosphere. The cell lines were bEnd.3 mouse cerebral endothelial cells (TfR-positive), HEY ovarian cancer cells (EpCAM-positive) and MOLT4 leukaemia cells (TfR-negative, EpCAM-negative). Cells were passaged (using 1× trypsin for adherent cells) when required for assays or as appropriate to maintain cell numbers.

TABLE 1

| Cells | Type | Properties | Growth medium |
|---|---|---|---|
| bEnd.3 | Mouse cerebral endothelial | Adherent | DMEM with low glucose (1 g/L) and 10% FCS |
| HEY | Human serous papillary ovarian adenocarcinoma | Adherent | DMEM with 10% FCS |
| MOLT4 | Human acute lymphoblastic leukaemia | Suspension | DMEM with 10% FCS |

Aptamers

Figure 14B:
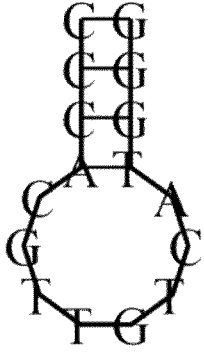
FIG. 14B shows additional sequences and structures of EpCAM aptamers and controls.
Figure 14B:
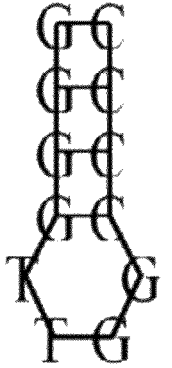
Figure 14B:
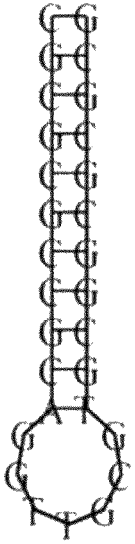
Figure 14B:
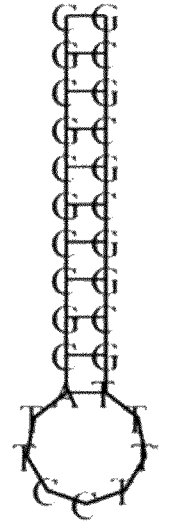

The aptamers are shown in FIGS. 14A and 14B. All aptamers were tagged with a 3' inv dT and a fluorophore on the 5' end (TYE 665). These were all commercially synthesised (Integrated DNA Technologies). Two different groups of aptamers were used. Four aptamers against the mouse TfR were initially tested. Following this, three conjugate aptamers, incorporating some of these anti-TfR aptamers and an anti-EpCAM aptamer (Ep7) derived from a larger EpCAM aptamer described in Song Y et al (2013) Analytical Chemistry 85(8):4141-9), were generated.

(SEQ ID NO: 16)
5' CAC TAC AGA GGT TGC GTC TGT CCC ACG TTG TCA TGG GGG GTT GGC CTG 3'

Two additional EpCAM aptamers were also produced designed Ep8 and Ep9 which were also derived from the larger EpCAM aptamer described in Song et al.

Characterisation of Aptamers i) Determining the Binding Affinity of the Aptamers

In order to determine the binding affinity (equilibrium dissociation constant $K_D$) of the aptamers. Binding assays were conducted to measure the binding to native EpCAM protein expressed on the cell surface. The aptamers were incubated with the cells at concentrations ranging from 0 nM to 400 nM. These were subsequently analysed by flow cytometry. Aptamers were thawed from storage (−20° C.) prior to use. These were then diluted via serial dilutions with phosphate buffered saline (PBS) in order to achieve the desired concentrations. PBS was supplemented with a $MgCl_2$ concentration appropriate for the aptamer (1 mM for anti-TfR aptamers; 5 mM for conjugate aptamers). Aptamers were then folded into their 3D structures using a thermocycler (85° C. for 5 minutes, slow cooling to 22° C. over 10 minutes and 37° C. for 15 minutes).

Concurrently, subcultured cells were incubated in blocking buffer (PBS with 10% FCS, 1 mg/mL BSA, 0.1 mg/mL tRNA) for 30 minutes. Following centrifugation, blocking buffer was removed and cells were resuspended in binding buffer (PBS with 10% FCS, 1 mg/mL BSA, 0.1 mg/mL tRNA). Cells (50 µL) were then incubated with the aptamers (50 µL) for 30 minutes at 37° C. at a range of concentrations (0 nM, 20 nM, 40 nM, 60 nM, 80 nM, 100 nM, 200 nM, 400 nM). Following this, cells were washed in 100 µL PBS three times before final resuspension for flow cytometry.

Aptamers were incubated with the chosen cell lines (bEnd.3 cells, mouse cells positive for TfR; HEY cells, human ovarian cancer cell line positive for EpCAM; and MOLT4 human cells negative for both TfR and EpCAM) at a range of concentrations. Aptamer-bound cells were analysed using a FACS Canto II flow cytometer (Becton Dickinson), counting 10,000 events for each sample, in order to determine the binding affinity of the aptamers. Viable cells exhibiting fluorescence were observed and the median fluorescent intensity was recorded. The value for the auto fluorescent 0 nM concentration was subtracted from the other figures to account for background fluorescence (Li N et al (2009) Journal of Proteome Research 8(5):2438-48). The resultant values were then used to determine the dissociation constant ($K_D$) via the Graph Pad Prism 3 software.

ii) Determination of Aptamer Internalisation into Cells

Confocal microscopy was used as a means of visualising aptamer internalisation into the cells. Both aptamers and cells were prepared in the same manner as described above before they were mixed and allowed to incubate at 37° C. The aptamers were used at a concentration of 200 nM and were allowed to incubate for 60 minutes. The concentration for the conjugate (bifunctional) aptamers was 400 nM and these were incubated with the cells for 120 minutes. Ten minutes prior to end of incubation, 2 µL of Hoechst nuclear stain (10 mg/mL) was added to cells. Cells were then washed three times with 100 µL of PBS as described above and resuspended in 20 µL ($8 \times 10^5$ cells/well) in an 8-chambered slide (Lab-Tek II, Nunc) for visualisation. Cells were incubated in blocking buffer for 60 mins followed by resuspension in binding buffer containing the aptamer and incubated for 60 mins at 37° C. Bisbenzimide Hoechst 33342 (3 mg/ml) (Sigma) was added to the cells during the final 10 min of incubation. The aptamer solution was removed and the cells were washed three times for 5 min each in PBS prior to visualisation using a FluoView FV10i laser scanning confocal microscope (Olympus).

In order to assess the mechanism of cellular uptake, the internalisation of a phycoethyrin-labelled rat anti-mouse TfR monoclonal antibody (R17217; Abcam) was also visualised by confocal microscopy by co-incubating it with the aptamer at 1 µg/mL for 30 minutes.

In Vitro Blood Brain Barrier Model

In order to assess the ability of the TfR containing aptamers to pass through an endothelial cell monolayer via receptor mediated transport (RMT) an in vitro model of the BBB was produced as shown schematically in FIG. 1. Transwell inserts (polyethylene terephthalate (PET) with 0.4 µm diameter pores) within a 24-well plate (Corning) were incubated with 100 µL of 50% Collagen IV for 2 hours at 37° C. Flasks of bEnd.3 cells were trypsinised to generate a single-cell suspension, and counted using a haemocytometer and trypan blue to ensure that a sufficient proportion of cells were alive. These were then centrifuged and resuspended in media. Wells were filled with 800 µL of serum-free media and transwell inserts were placed on top. Cells were then seeded in 90 µL of serum-free media at a density of $1 \times 10^6$ cells/cm² and were allowed to incubate at 37° C. Cells were allowed to settle for 6 hours and then 60 µL of enhanced media (DMEM low glucose: Ham's F12 (1:1), (both serum-free) 550 nM hydrocortisone, 32 µM cAMP, 17.5 µM aminophylline, 1 µM retinoic acid, 5 µg/mL insulin, 2.75 µg/mL transferrin, 2.5 ng/mL sodium selenite, 100 ng/mL bFGF (basic fibroblast growth factor), 20 ng/mL EGF (epidermal growth factor)) (Wuest D M et al (2013) Journal of Neuroscience Methods 212(2):211-21) was added to the transwells. Media in both compartments were replaced the next day with enhanced media in order to supplement the growth of the monolayer.

(i) Transendothelial Electrical Resistance Measurements

In order to assess the integrity of the membrane, the transendothelial electrical resistance (TEER) of the transwells was measured. The electrodes of an EVOM2 Epithelial Voltohmmeter (World Precision Instruments) were inserted into both chambers of the BBB model and the resistance was recorded in ohms. This value was then multiplied by the area of the transwell. The same was then performed using a blank transwell insert and subtracted from the previously recorded value in order to obtain the TEER in Ωcm2.

(ii) Visualisation of Transwell Membranes

Transwells were aspirated of media before being gently rinsed with PBS. Methanol was then added into the transwells for 5 minutes in order to fix the cells. This was then removed and haematoxylin was added for 5 minutes. Transwells were subsequently rinsed with PBS and then acidified alcohol was added. After another rinsing with PBS, eosin was added to the transwells for 30 seconds. Transwells were visualised under a light microscope (Olympus) before and after haematoxylin and eosin staining.

(iii) HEY-bEnd.3 Co-Culture and Aptamer Blood Brain Barrier Permeability

HEY cells were subcultured and counted using a haemocytometer and trypan blue in order to assess the percentage of living cells. Subsequently, they were diluted in DMEM media at a concentration of 87 500 cells/mL. Media was removed from the bottom compartment of the in vitro BBB model and replaced with 800 µL of the HEY cell solution, seeding at 70 000 cells per well. These were allowed to incubate overnight. Next, media was removed from the upper compartment of the transwells and 100 µL of aptamer at a concentration of 2 µM was pipetted on top of the transwell membrane. Following a three hour incubation at 37° C., media in the bottom compartment was removed and centrifuged. Cells were then resuspended in 100 µL of PBS and 2 µL of Hoechst nuclear stain (10 mg/mL) was added and allowed to incubate for ten minutes. Cells were then washed three times in 100 µL of PBS before viewing under a confocal microscope (Olympus).

Data Analysis

Data and results were analysed using GraphPad Prism 3 and reported as mean and standard error of the mean (mean±S.E.M.) unless otherwise stated.

Example 1 Characterisation of Anti-Transferrin Receptor Aptamers (i) TfR Aptamer Generation The transferrin aptamers generated herein were derived from an aptamer against mouse transferrin receptor (tfR) as previously described in Chen et al (2008) PNAS 105(41): 15908-13 and shown in FIGS. 3A and B. This original aptamer design was used as a proof-of-concept for the transcytosis of an aptamer through the BBB. The inventors further truncated the original TfR aptamer of Chen et al and having the sequence (SEQ ID NO: 15)
5' GAATTCCGCGTGTGCACACGCTCACAGTTAGTATCGCTACGTTCTTT

Figure 2:
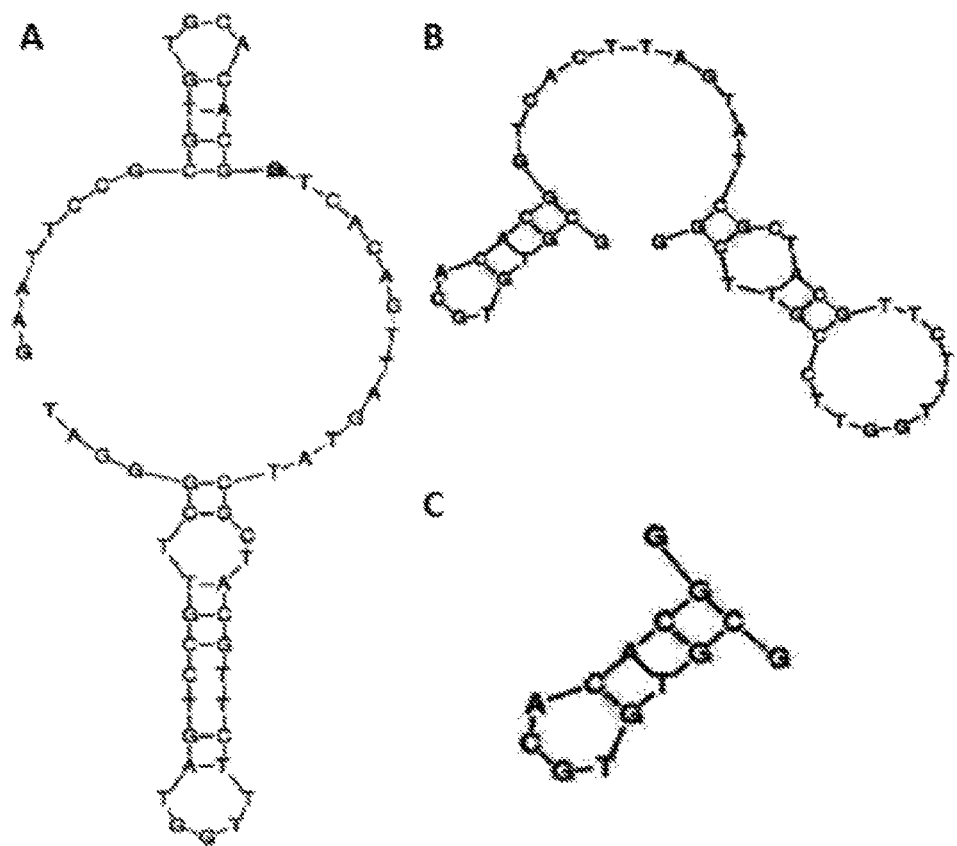
FIG. 2 shows a schematic describing the truncation of the original anti-transferrin receptor aptamer. The original aptamer (A) (SEQ ID NO: 15) was selected after six rounds of SELEX. This was truncated it to a shorter aptamer fifty base pairs long (B) (SEQ ID NO: 17). This was further truncated by the inventor to a length of fourteen nucleotides to produce TfR1 (C) (SEQ ID NO: 18).

GGTAGTCCGTTCGGGAT 3' aptamer to generate the TfR aptamer (FIG. 2C and SEQ ID NO:4)). This was then subsequently modified via the scrambling of the sequence of the binding loop to produce three alternate versions (designated TfR2, TfR3 and TfR4) as shown in FIG. 14A. The 2D structure of the anti-TfR aptamers was predicted with the VIENNA software (Gruber A R et al (2008) Nucleic Acids Research 36 (Web server issue):W70-W4 so as to ensure that it was unchanged following the alteration of the sequence in the binding loop.

(ii) Determination of Anti-Transferrin Receptor Aptamer Binding Affinity

The binding affinity of an aptamer to a target receptor is an important characteristic of the molecule that has a significant impact on its use as a therapeutic. Higher affinities enable a greater uptake into a cell, but can also prevent the optimal therapeutic distribution of a drug throughout a tumour and can risk off-target effects. In addition, some aptamers require only a transitory binding in order to carry out the function for which they were intended. This is the case with the anti-TfR aptamers being designed herein. As these are being engineered so as to transcytose through the BBB, and not simply to become internalised into the endothelial cells, a lower binding affinity is necessary.

The binding affinities of aptamers TfR1, TfR2, TfR3 and TfR4 were determined semi-quantitatively via flow cytometry, using bEnd.3 mouse cerebral endothelial cells as a Tf R-positive cell line and MOLT4 acute lymphoblastic leukaemia cells—which express the human TfR, but not the mouse TfR (Sutherland R et al (1981) PNAS 78(7):4515-9)—as a negative control. Three independent binding assays were performed for each aptamer against each cell line.

The binding assay results indicate that the changes made in the aptamer binding loop had a varied impact on the binding affinity, although not to the extent that any aptamer completely lost specificity. Surprisingly, the aptamer with the lowest binding affinity was the original truncation, TfR1 (FIG. 3A; KD=5764±7117 nM), in contrast to the aptamer that exhibited the tightest binding, TfR3 (FIG. 3C; KD=365.6±83.28 nM).

The binding affinity of the aptamers was also measured against a human cell line (MOLT4) as a negative control. Although MOLT4 does express TfR, there was not expected to be any specific binding, as the amino acid sequence homology between the human and mouse TfR is only 77% (Altschul S F et al (1990) Journal of Molecular Biology). The aptamers did display non-specific binding to the MOLT4 cells, establishing confidence that the binding observed against the bEnd.3 cells was indeed specific.

(iii) Quantitative Analysis of Anti-Transferrin Receptor Aptamer Internalisation into Cells The uptake of these aptamers into cells is an important factor in determining the potential for use as therapeutics. The anti-transferrin receptor aptamers generated herein are designed to pass through the BBB via the active transcytosis pathway. Hence, it is critical to ensure that the aptamers are being internalised into cells instead of merely attaching to the cell surface. This was done by visualising the internalisation of aptamers at a concentration of 200 nM into bEnd.3 and MOLT4 cells over the course of a one hour incubation with confocal microscopy.

All four anti-TfR aptamers were taken up into the TfR-positive mouse cerebral endothelial cells. The TfR-negative cells did not show any clear aptamer uptake, establishing confidence in the specificity of the internalisation process. In addition, the internalised aptamer had a punctate staining pattern, highlighting a possible endosomal localisation, which is indicative of active cellular uptake.

(iv) Determination of the Specificity of Anti-Transferrin Receptor Aptamer Uptake Aptamers are relatively new molecular tools in the field of diagnostics and therapeutics. Hence, despite their many advantages over protein-based binding molecules (see Table 1), antibodies are a more well-accepted approach to targeting cells via specific surface antigens. The performance of the aptamer with a corresponding antibody was compared by examining uptake in bEnd.3 cells. This was done by incubating the highest affinity aptamer, TfR3, and the anti-TfR antibody with the bEnd.3 cells and observing them via confocal microscopy.

Co-localisation of the TfR3 aptamer with the anti-TfR antibody in bEnd.3 cells was observed by microscopy. A very similar distribution pattern was observed with the aptamer and the antibody throughout the cell, providing an indication that both molecules entered the cell via the same pathway.

(V) Qualitative Time Course Analysis of Anti-Transferrin Receptor Aptamer Internalisation into Cells The anti-TfR aptamers generated herein are intended to be used as drug delivery agents capable of crossing the blood-brain barrier (BBB). In an in vivo or clinical setting, these would need to pass from the bloodstream and into the BBB endothelial monolayer before exiting on the other side into the brain parenchyma. Given this, it is vital that these are not only capable of entered cells via active transport processes, but can also exocytose out again. Therefore, a time course internalisation experiment was conducted in order to establish whether or not the aptamers are being retained in the cells or are returning to the extracellular fluid. The best binder to the transferrin receptor, TfR3, was incubated with bEnd.3 cells across six different time points (0.5, 1, 2, 4, 6, 8 hr). The cells were then viewed with a confocal microscope.

Figure 3:
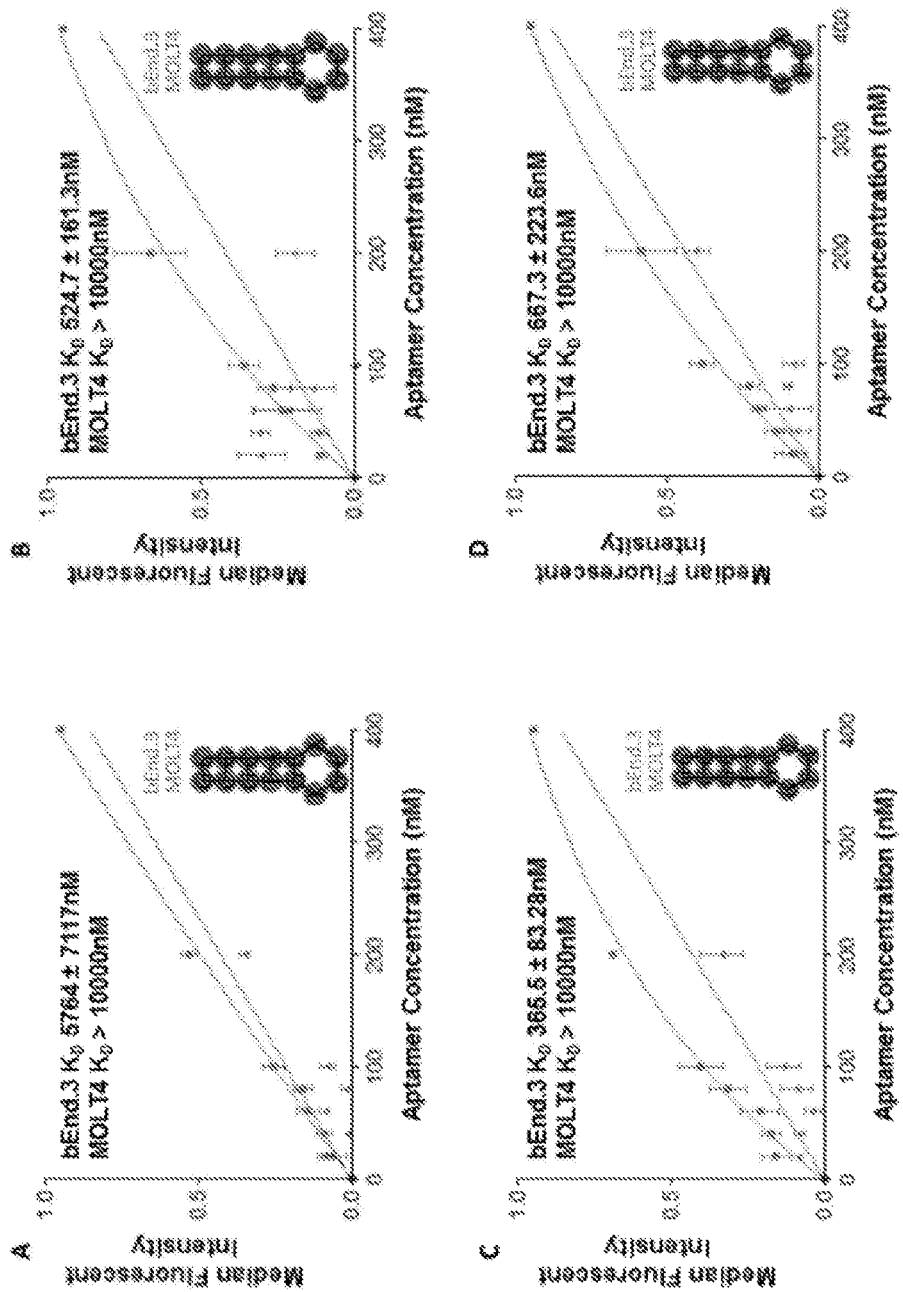
FIG. 3 shows determination of the $K_D$ of anti-TfR aptamers with TfR-positive (bEnd.3) and—negative (MOLT4) cells. The top curve in each case corresponded to bEnd.3 cells and the lower curve to MOLT4 cells. Binding curves were obtained using concentrations 0, 20, 40, 60, 80, 100, 200 and 400 nM. The construct used is indicated in the figure. (A) TfR1; (B) TfR2; (C) TfR3; (D) TfR4. Data presented as median fluorescent intensity±standard error of the mean (n=3).

Similar patterns of internalisation were seen across each time point consistent with previous results, with both sets of experiments showing an even distribution and punctate appearance. FIG. 3 shows that this distribution pattern was maintained throughout the eight hours of incubation, indicating that the aptamer was not removed from the cells.

Example 2 Characterisation of EpCAM Aptamers

Figure 4:
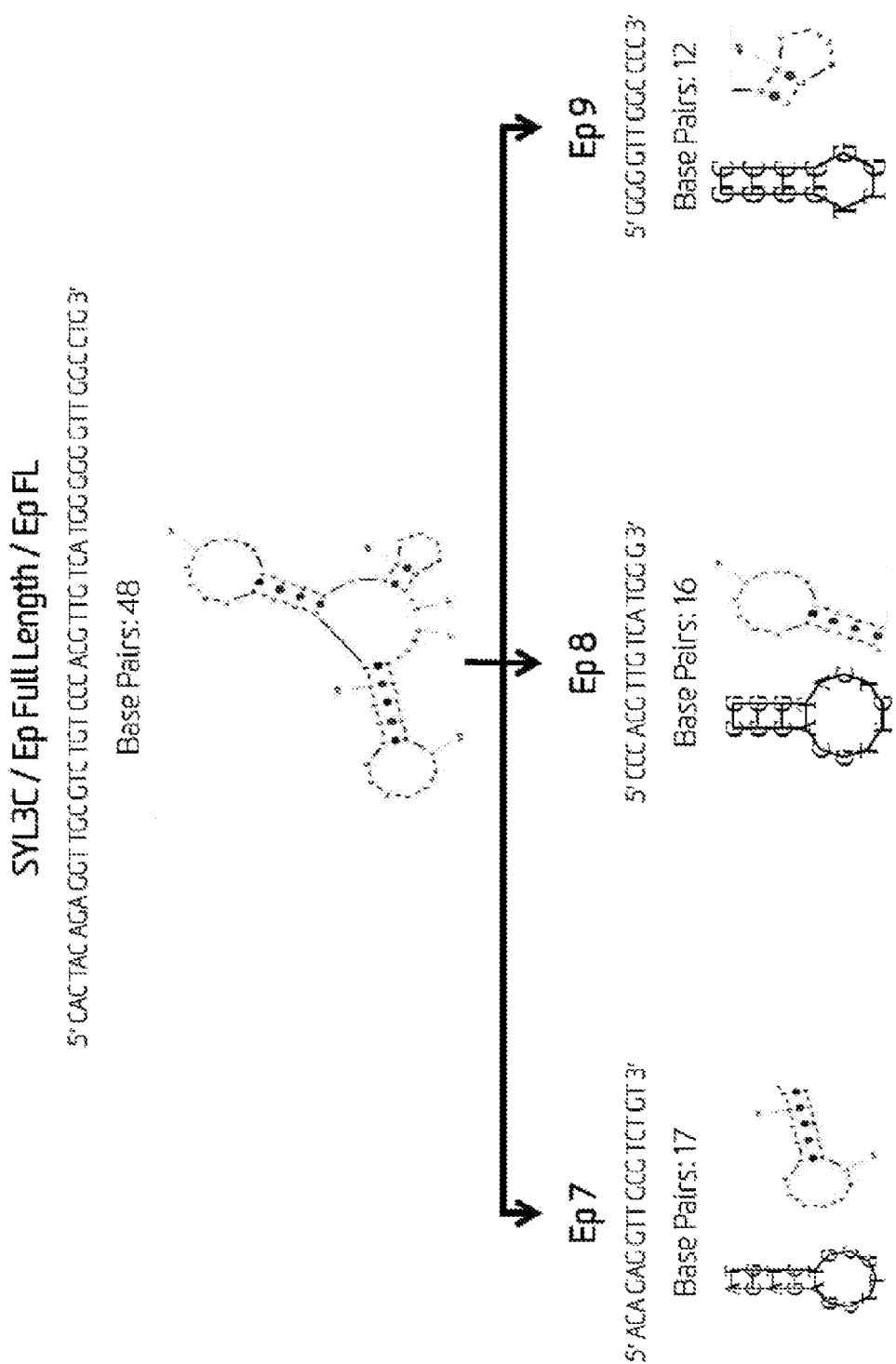
FIG. 4 shows the full length DNA EpCAM aptamer (SEQ ID NO: 16) and truncated Ep7 (SEQ ID NO: 9), Ep8 (SEQ ID NO: 11), and Ep9 (SEQ ID NO: 12) aptamer structures.

The SYL3C (Full length or FL) 48 mer aptamer was originally generated by Song et al (2013) Analytical Chemistry 85:4141-4149. 2D structures were predicted using RNAfold. Truncated versions of this aptamer designated Ep7, Ep8 and Ep9 respectively were generated as shown in FIG. 14A, FIG. 14B, and FIG. 4. Sequences of the extended Ep7 and scrambled extended Ep7 aptamers are shown in FIG. 14B. The extended Ep7 has the same binding loop as Ep7 and the scrambled extended Ep7 has randomly selected base pairs in the binding loop. 2D structures were predicted using RNAfold (Gruber A R et al. (2008) The Vienna RNA websuite. Nucleic acids Research 36:W70-W4.

All aptamers including truncated Ep7, Ep8, Ep9, Extended (Ex) ExEp7, and Scrambled (Scr) ScrEx Ep7 were commercially synthesized (Integrated DNA Technologies) with a TYE665 dye at the 5' end and an inverted thymidine at the 3' end.

i) Determination of Binding Affinity

The equilibrium dissociation constant (KD) of each DNA EpCAM aptamer (Ep7, Ep8 and Ep9) was determined by measuring its binding to native EpCAM protein expressed on the cell surface using flow cytometry. HT29, HEY and HEK293T ($5 \times 10^5$) cells were first incubated with blocking buffer (PBS containing 10% FCS, 1 mg/mL tRNA, 1 mg/mL BSA) for 30 minutes followed by a single wash with binding buffer (PBS containing 10% FCS, 1 mg/mL tRNA, 1 mg/mL BSA) prior to incubation with serial dilutions of concentrations of the respective TYE665-labelled aptamers (0 to 200 nM) in binding buffer for 30 min at 37° C. The cells were washed three times with PBS and resuspended in PBS prior to flow cytometric analysis. The fluorescent intensity was determined using a FACS Canto II flow cytometer (Becton Dickinson), counting 10,000 events for each sample. The mean fluorescent intensity of each concentration was subtracted from that of the auto fluorescent control and the $K_D$ for each aptamer was calculated from the normalised values for fluorescent intensity.

Figures 1, 5A:
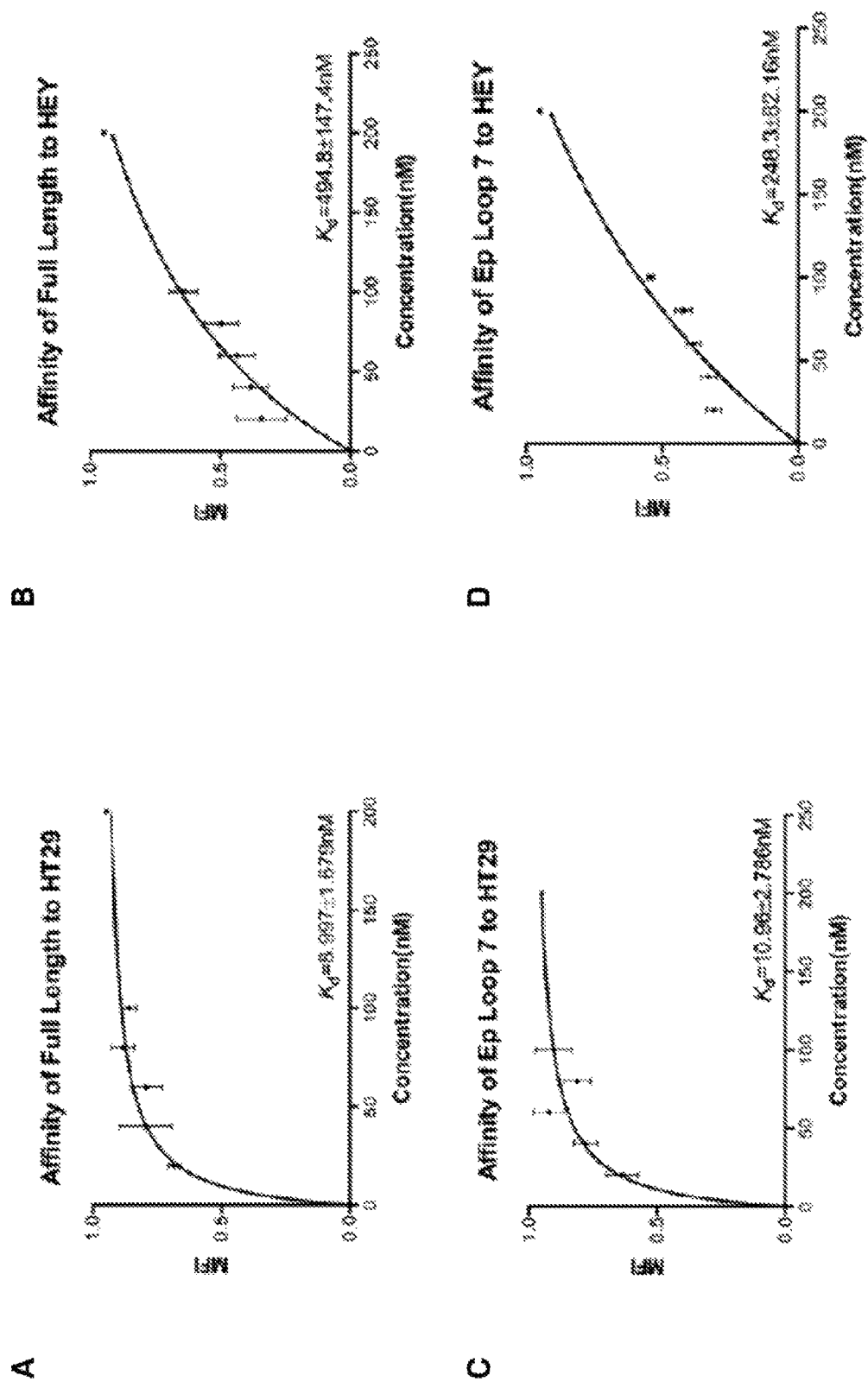
Figures 2, 5A:
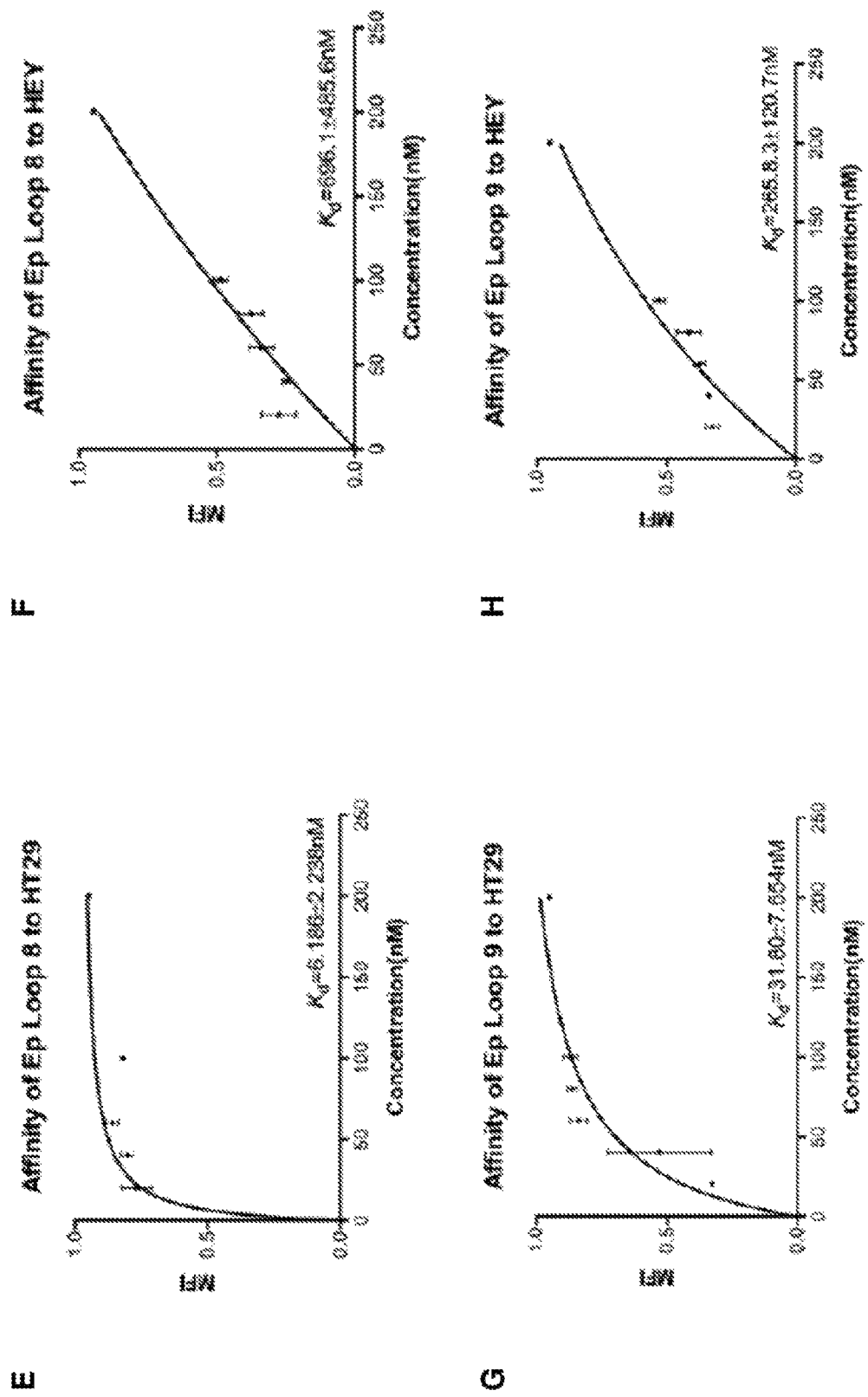

FIG. 5A shows the determination of the equilibrium dissociation constants (KD) for the interaction of Ep7, Ep8 and Ep9 against EpCAM positive cell lines, HT29 and HEY compared with the full length Song et al aptamer (SEQ ID NO: 16).

Figure 5B:
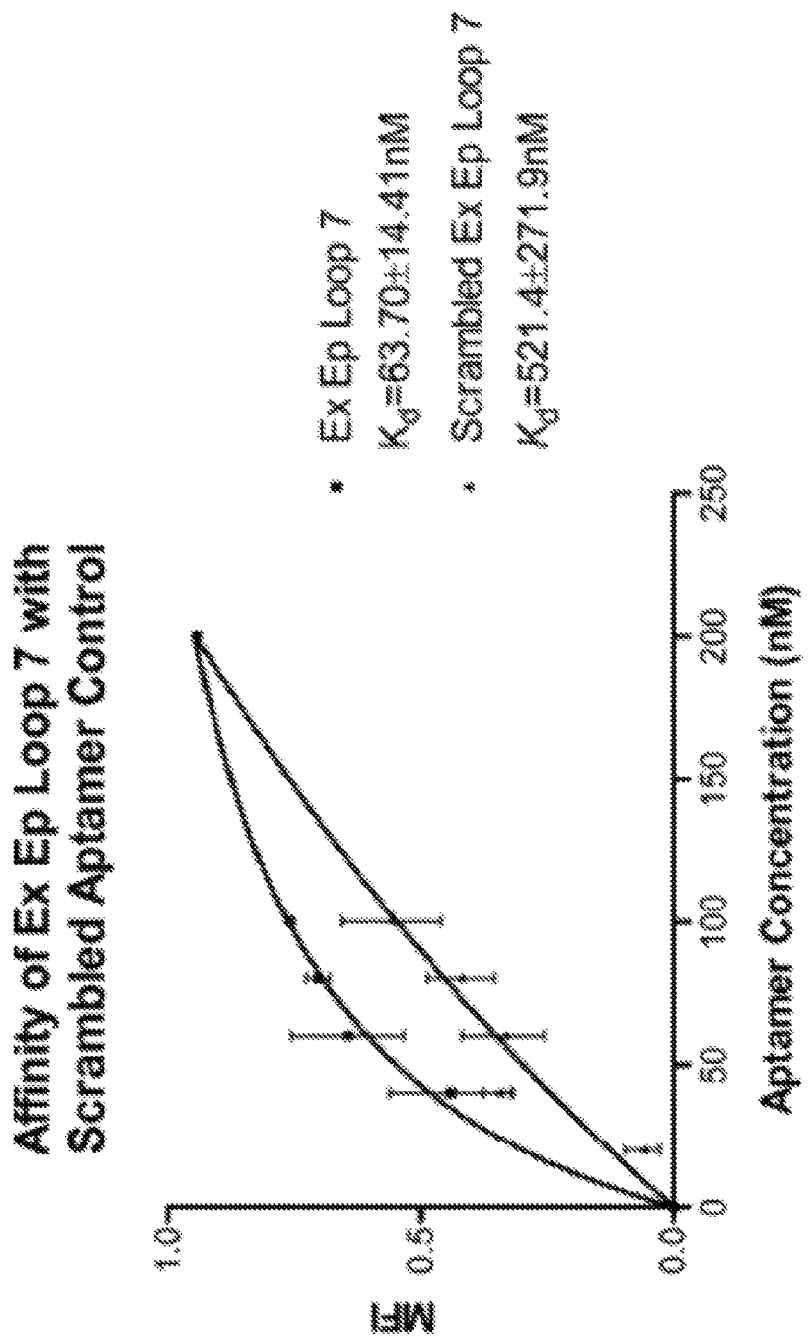
FIG. 5B shows determination of equilibrium dissociation constants (KD) for the interaction of extended Ex Ep 7 and Scrambled Ex Ep 7 against EpCAM positive ovarian cancer cell line, HEY. Fluorescent histograms were determined at 0 and 100 nM of EpCAM DNA aptamers using a cell density of 5×105 cells/mL.

FIG. 5B shows the determination of equilibrium dissociation constants ($K_D$) for the interaction of EX Ep7 and Scr Ex Ep7 aptamers against EpCAM positive ovarian cancer cell line, HEY.

The $K_D$ values for each aptamer is provided in Table 3 below as median±SEM (n=3):

TABLE 3

Equilibrium dissociation constants of truncated EpCAM aptamers

| Aptamer Type | Cell type | KD value (nM) |
|---|---|---|
| Full length EpCAM aptamer (SEQ ID NO: 15) | HT29 | 8.997 ± 1.679 |
|  | HEY | 494.8 ± 147.2 |
| Ep7 aptamer (SEQ ID NO: 9) | HT29 | 10.96 ± 2.786 |
|  | HEY | 248.3 ± 82.16 |
| Ep8 aptamer (SEQ ID NO: 11) | HT29 | 6.186 ± 2.238 |
|  | HEY | 696.1 ± 485.6 |
| Ep9 aptamer (SEQ ID NO: 12) | HT29 | 31.80 ± 7.654 |
|  | HEY | 265.8 ± 120.7 |
| Ex Ep7 aptamer (SEQ ID NO: 13) | HEY | 63.70 ± 14.41 |
| Scr Ex Ep7 aptamer (SEQ ID NO: 14) | HEY | 521.4 ± 271.9 |

Results show that the truncated aptamers maintained specificity and sensitivity towards EpCAM.

Figure 6A:
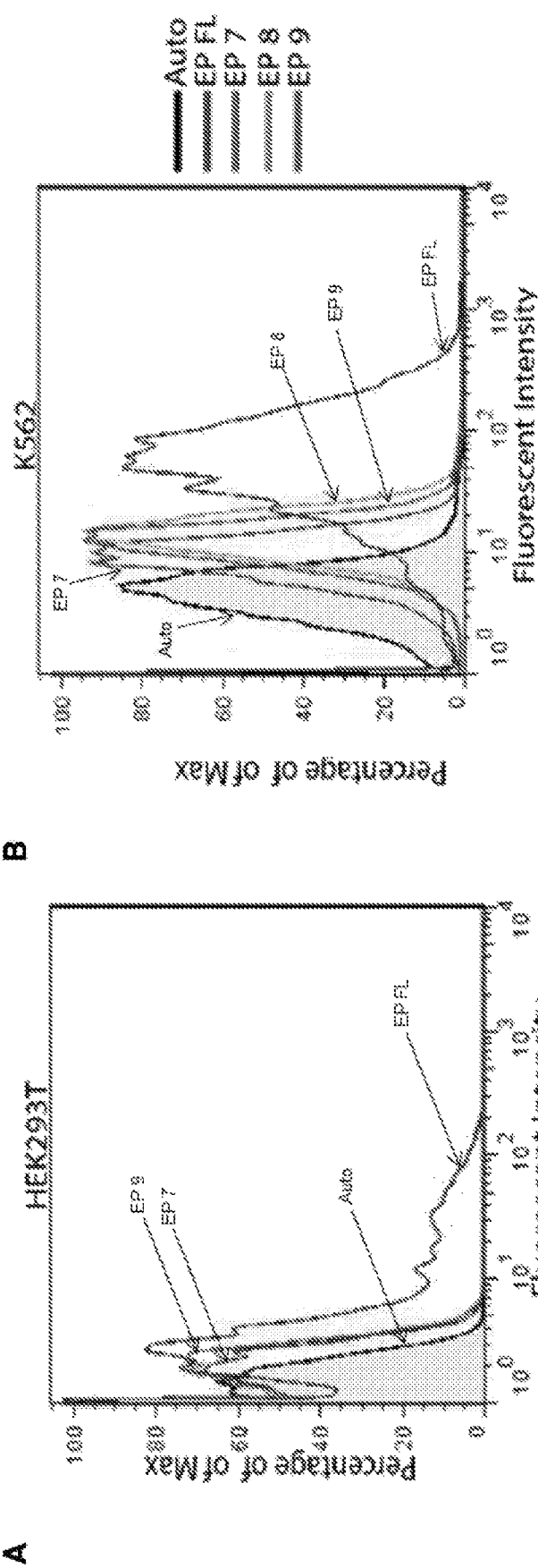
FIGS. 6A and B shows determination of equilibrium dissociation constants (KD) for the interaction of truncated loops against EpCAM negative cell lines, HEK293T and K562. Representative fluorescent overlays are shown at 0 nM (Auto) and 100 nM of EpCAM DNA aptamers using a cell density of 5×105 cells/mL.
Figure 6B:
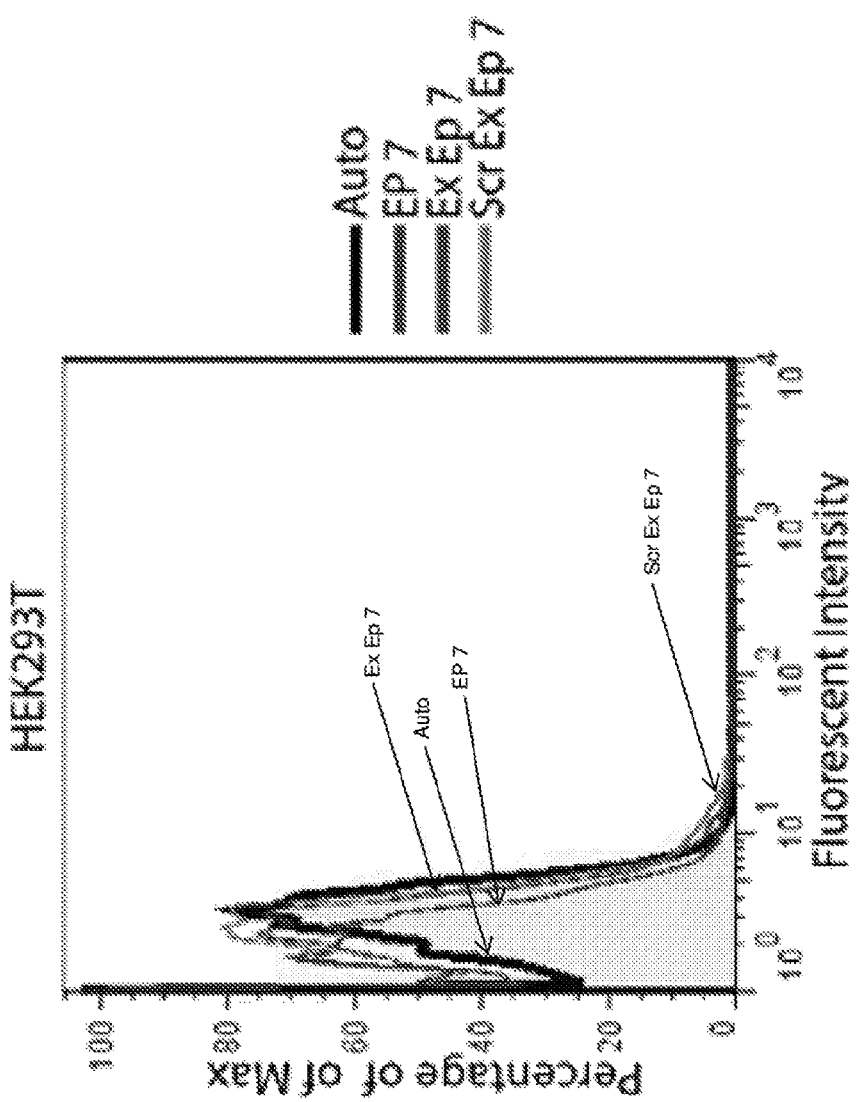

FIG. 6A shows determination of equilibrium dissociation constants ($K_D$) for the interaction of Ep7, Ep8 and Ep9 against EpCAM negative cell lines, HEK293T and K562. FIG. 6B shows determination of equilibrium dissociation constants ($K_D$) for the interaction of extended Ex Ep 7 and Scrambled Ex Ep 7 against EpCAM positive ovarian cancer cell line, HEY.

These results show that the aptamers Ep7, Ep8 and Ep9 did not bind to EpCAM negative cell lines.

ii) Internalisation Assay

The ability of each DNA EpCAM aptamer to be internalised was established through confocal microscopy.

HT29, HEY, K652 and HEK293T were seeded at 8×10⁵ cells per well in 8-chamber slide for 24 h in preparation for confocal microarray. Cells were incubated with blocking buffer for 60 min, followed by resuspension in binding buffer and containing 200 nM EpCAM aptamer or negative control aptamer and incubated for 60 min at 37° C. Bisbenzimide Hoechst 33342 (3 mg/ml) (Sigma) was added to the cells during the final 10 min of incubation. The aptamer solution was removed and the cells were washed three times for 5 min each in PBS prior to visualisation using a FluoView FV10i laser scanning confocal microscope (Olympus).

Figure 7:
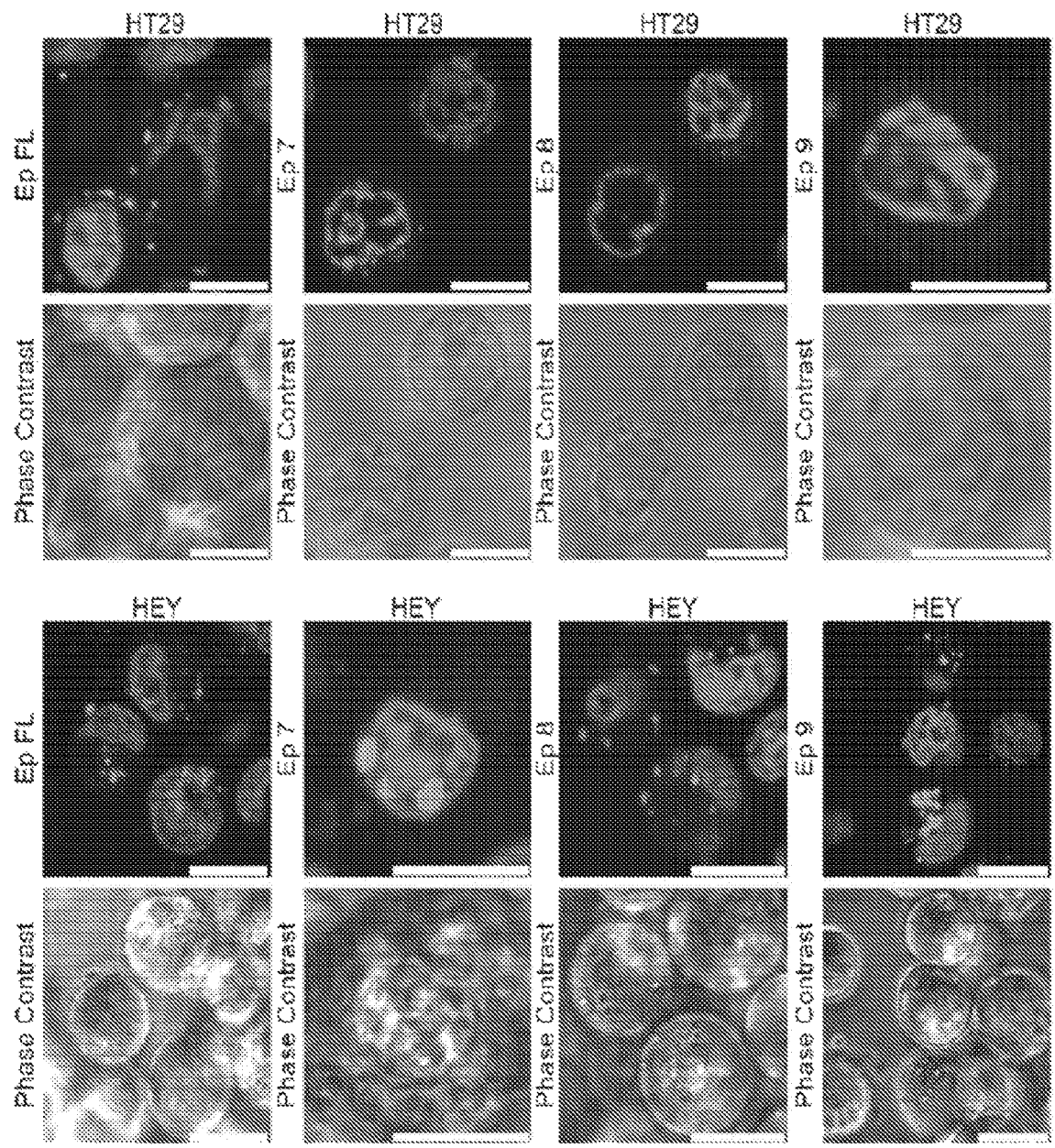
FIG. 7 shows confocal images of cultured HT29 and HEY cells stained with TYE665-labelled aptamers. Ep Full Length, Ep 7, Ep 8 and Ep L9 aptamers and Hoechst 33342. Scale bar=10 μm.

FIG. 7 shows the results of confocal images of cultured HT29 and HEY cells stained with TYE665-labelled aptamers (Ep7, Ep8 and Ep9). Scale bar=10 μm. The results show that the truncated aptamers were internalised by EpCAM positive cells.

Figure 8:
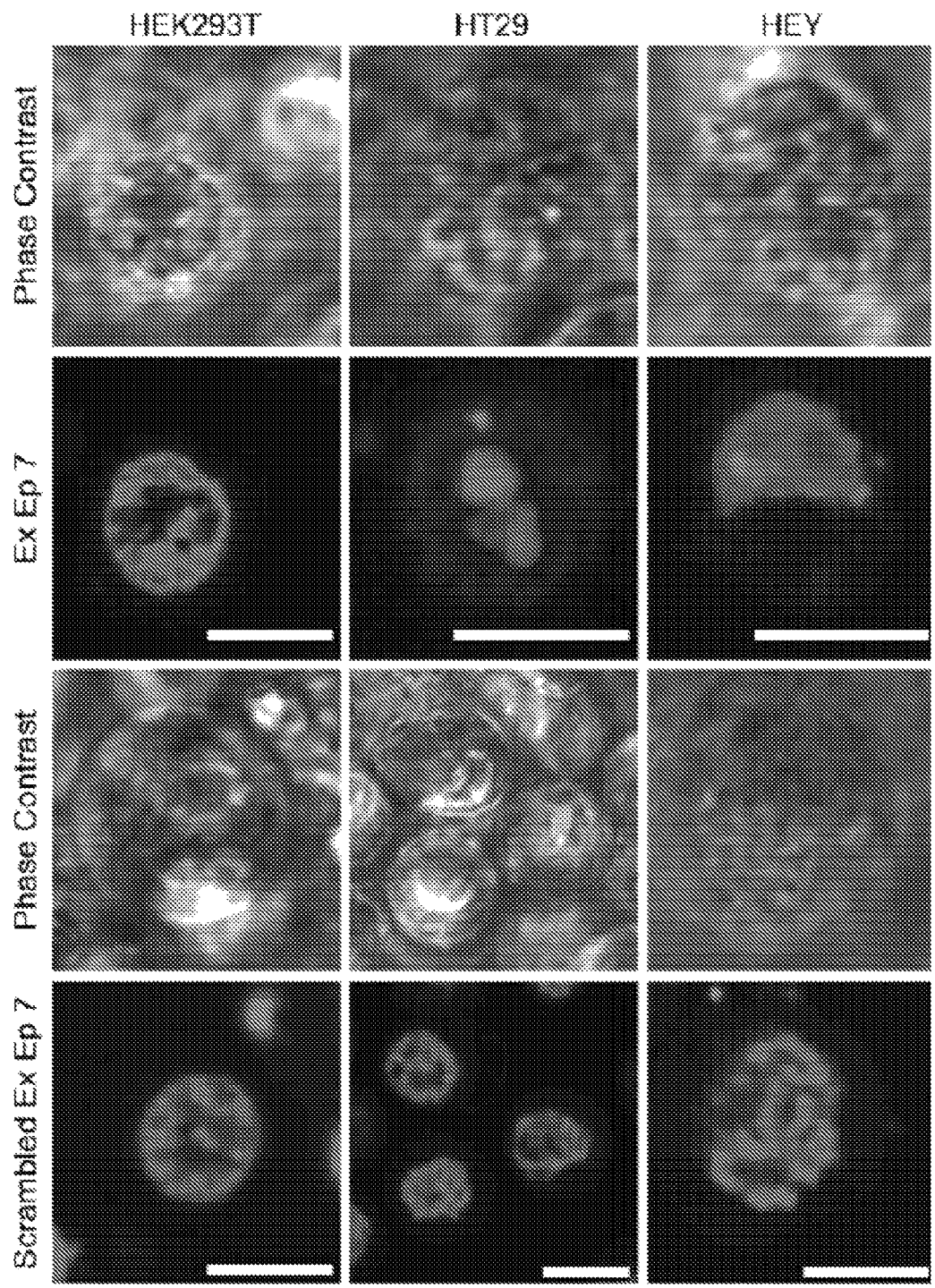
FIG. 8 shows confocal images of cultured HEK293T, HT29 and HEY cells stained with TYE665-labelled aptamers. Ex Ep 7 and Scr Ex Ep 7 aptamers and Hoechst 33342. Scale bar=10 μm

FIG. 8 shows confocal images of cultured HEK293T, HT29 and HEY cells stained with TYE665-labelled aptamers (Ex Ep 7 and Scr Ex Ep 7). The results show that the extended EXEp7 was internalised however the scrambled Ex Ep7 aptamer was not internalised.

iii) Determination of Doxorubicin Loading Efficiency

The anthracycline class of drugs, including DOX, have fluorescence properties that become quenched after intercalation into DNA (Valentini L et al (1985) Il Farmaco edizione scientifica 40(6):377-90. The natural fluorescence of doxorubicin and its subsequent quenching after intercalating with the DNA EpCAM aptamers was utilised for the measurement of the extent of doxorubicin conjugation via Fluorescent Spectroscopy. The conjugation process was studied using different aptamer-doxorubicin molar ratios (0, 0.01, 0.04, 0.08, 0.1, 0.2, 0.3, 0.4, 0.5, and 0.6) and analysed with a fluorescence plate reader based on a standard curve of free doxorubicin.

Prior to conjugation, aptamers were prepared for application as previously described. DOX was then combined with aptamer in conjugation buffer containing 0.1 M sodium acetate, 0.05 M NaCl, and 5 mM $MgCl_2$ and incubated at 37° C. in an Orbital mixer/incubator (RATEK) for 1 hour with agitation (75 r.p.m). The conjugate was then passed through a Sephadex®G-10 medium column (Sigma-Aldrich) to separate the aptamer: doxorubicin conjugate from free DOX. As DOX has a natural fluorescence which is subsequently quenched following intercalation into double stranded DNA, this characteristic of DOX was exploited to determine the amount of DOX that was intercalated into the double stranded stem region of the conjugate aptamers. After column separation, DOX was extracted from the conjugate yield by adding 150 uL of acetonitrile. This solution was then centrifuged for 5 min at 21,000 g. Eighty microliters of supernatant was removed and fluorescent intensity was quantified with a fluorescent plate reader. A calibration standard curve was prepared with known concentrations of DOX under the same condition Data was analysed using Graph Pad Prism 3 and data was reported as mean and standard error of the mean (mean±SEM) unless otherwise stated.

The molar ratio of each aptamer to doxorubicin was determined and is shown in Table 4 below.

TABLE 4

| Aptamer | ratio of aptamer to dox |
|---|---|
| | Molar ratio aptamer:dox |
| EpCAM full length aptamer (SEQ ID NO: 15) | 0.53 ± 0.13 |
| Ep7 aptamer (SEQ ID NO: 9) | 0.42 ± 0.11 |
| Ep8 aptamer (SEQ ID NO: 11) | 0.38 ± 0.06 |
| Ep9 aptamer (SEQ ID NO: 12) | 0.35 ± 0.06 |
| ExEp7 aptamer (SEQ ID NO: 13) | 1.17 ± 0.02 |
| ScrExEp7 aptamer (SEQ ID NO: 14) | 1.01 ± 0.01 |

The full length and truncated aptamers were able to intercalate doxorubicin.

Example 3 Characterisation of Conjugate Aptamers (i) Conjugate Aptamers

An aptamer against EpCAM had previously been generated by Song et al (2013) Analytical Chemistry 85:4141-4149. A truncated version of this (designated Ep7, FIG. 14A), which had previously been characterised in the inventor's lab, was used to conjugate with the anti-TfR aptamers in order to produce three bi-specific aptamers for characterisation. The sequences of the bifunctional aptamers are shown in FIG. 14B. The binding loops of each of TfR and Ep7 were scrambled. Bi1 was based on TfR1 and Ep7, Bi2 was based on TfR2 and Ep7 and Bi3 was based on TfR3 and Ep7.

Minor changes were made in the stem region to increase the number of GC pairs, in anticipation of the intercalation of the aptamers with doxorubicin. The 2D structure of the bi-specific aptamers was determined, again, with the VIENNA software in order to establish whether or not the shape of the two original aptamers was retained in the conjugate.

(ii) Determination of Conjugate Aptamer Binding Affinity

As is well-documented in the literature and had already been observed in this study with the anti-TfR aptamers, even minor changes to the composition of an aptamer can alter the binding properties. Given the more substantial changes made to the original aptamers in order to generate the conjugates, it was critical to determine the extent to which the binding affinity to both TfR- and EpCAM-expressing cells had deviated.

The binding affinities of aptamers Bi1, Bi2 and Bi3 were determined semi-quantitatively via flow cytometry, using bEnd.3 cells to assess reactivity with TfR, HEY cells to determine EpCAM specificity and the MOLT4 cell line as a negative control. Three independent binding assays were performed for these aptamer against all three cell lines (bEnd.3, HEY and MOLT4).

Figures 1, 9:
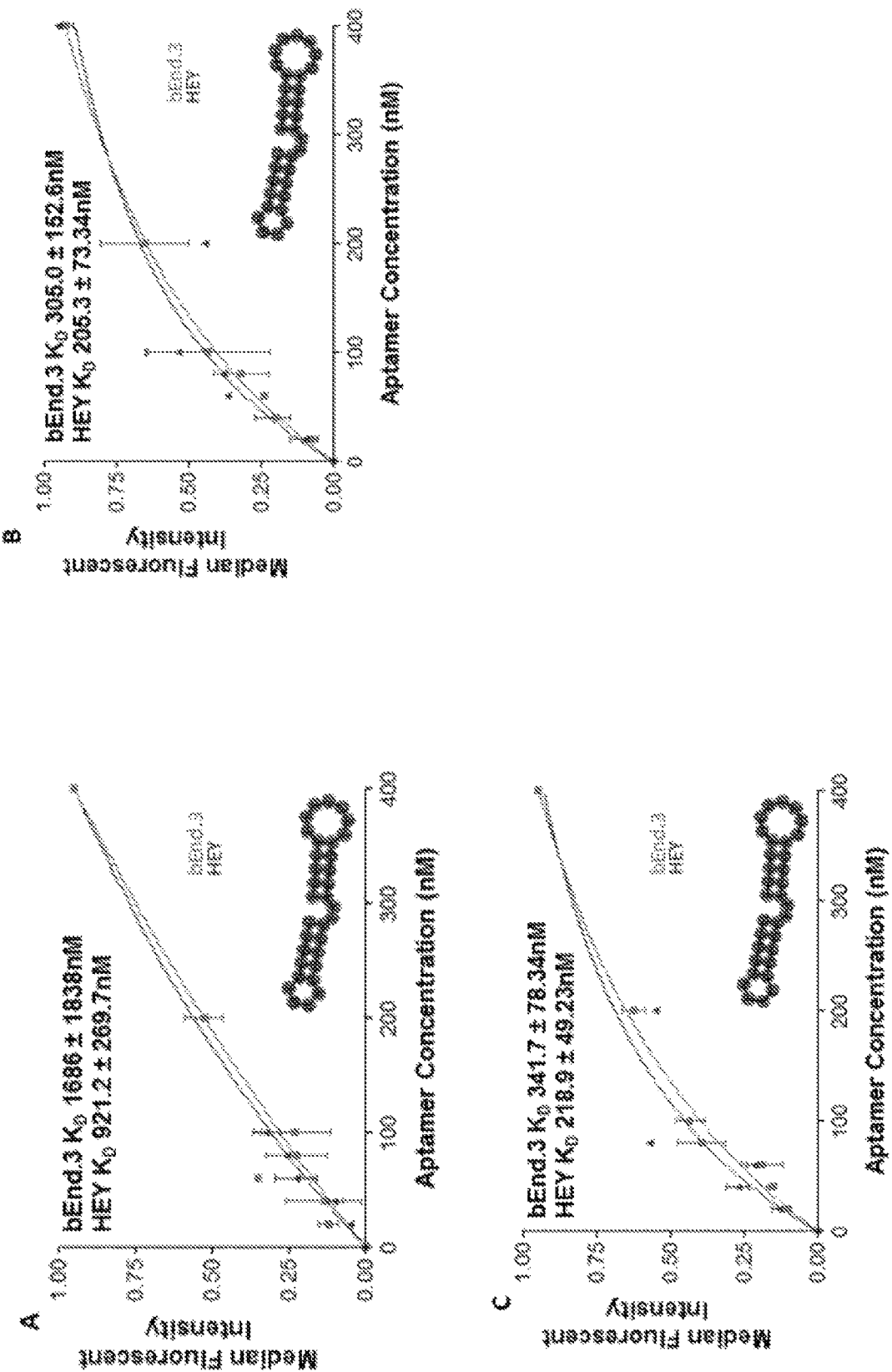
Figures 2, 9:
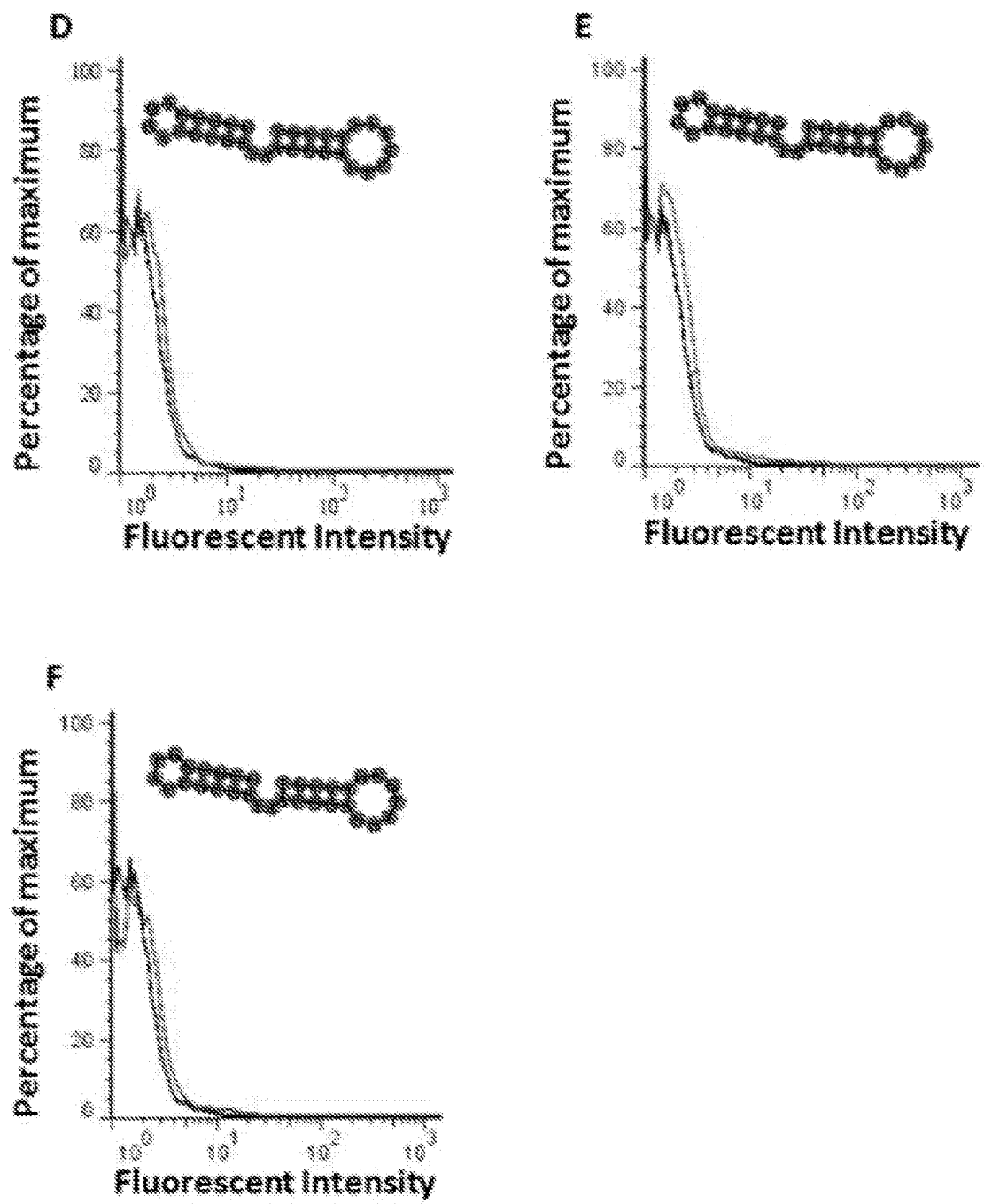

The binding curves for the conjugate aptamers revealed specific binding against both positive cell lines (FIG. 9A-C). Indeed, the binding affinities for the conjugate aptamers were similar to, if not stronger than, those of the single aptamers from which they were designed (Table 5). When considering the affinity to the bEnd.3 cells, Bi2 (FIG. 9B; KD=305.5±152.6 nM) was a significantly tighter binder than the single aptamer on which it was based, TfR2 (Table 5; KD=524.7±161.3 nM). In addition, the other two conjugate aptamers displayed binding affinities within the range of the of the two anti-TfR aptamers that shared the same respective binding loops. Against the EpCAM-expressing HEY cells, both conjugate aptamers that contained the same binding loop as the Ep7 aptamer had a similar binding affinity to those previously recorded (KD=248.3±82.16 nM).

In contrast, Bi1, which had the scrambled EpCAM binding loop, had a much weaker binding affinity (FIG. 9A; KD=921.2±269.7 nM).

TABLE 5

Comparison of the binding affinities of the conjugate aptamers with the constituent aptamers

| Single Aptamer | KD (nM) | Conjugate Aptamer | KD (nM) |
|---|---|---|---|
| bEnd.3 (TfR-positive) | | | |
| TfR1 | 5764 ± 7117 | Bi1 | 1686 ± 1838 |
| TfR2 | 524.7 ± 161.3 | Bi2 | 305.0 ± 152.6 |
| TfR3 | 365.5 ± 83.28 | Bi3 | 341.7 ± 78.34 |
| HEY (EpCAM-positive) | | | |
| (Not analysed) | — | Bi1 | 921.2 ± 269.7 |
| Ep7 | 248.3 ± 82.16 | Bi2 | 205.3 ± 73.34 |
| Ep7 | 248.3 ± 82.16 | Bi3 | 218.9 ± 49.23 |

No binding of the conjugate aptamers was observed against the MOLT4 negative cell line. This is in contrast to the previous results with the anti-TfR aptamers against these cells, which demonstrated binding that was non-specific (FIG. 3). This is evident in that no shift in population fluorescence was observed between the 0 nM and 100 nM aptamer concentrations (FIG. 9D-F).

(iii) Quantitative Analysis of Conjugate Aptamer Internalisation into Cells

As with the anti-TfR single aptamers, it was necessary to ensure that the binding that had been observed could be attributed to cellular internalisation rather than surface attachment. This was done in a similar manner as before. The internalisation of the conjugate aptamers was visualised at a concentration of 400 nM into bEnd.3, HEY and MOLT4 cells over the course of a two hour incubation with confocal microscopy.

As observed by confocal microscopy, all three conjugate aptamers were observed to become internalised into the EpCAM-positive HEY cell line. In contrast, only aptamers Bi2 and Bi3 were internalised into the TfR-expressing bEnd.3 cells. Again, a punctate distribution of staining was present inside the cells that took up aptamer. No internalisation was observed in the MOLT4 negative control.

(iv) Determination of EpCAM Specificity of the Conjugate Aptamers Against the HEY Cell Line Given that the conjugate aptamers have been observed to bind to two different targets, it was unclear whether the results obtained against the HEY cell line from either the binding assays or from confocal microscopy were due to EpCAM binding or were because of any TfR present of these cell lines. Indeed, the expression of TfR is ubiquitous in human tissue Harel E et al (2011) PLoS ONE 6(9): e24202. Hence, it was also important to ensure that a mouse anti-TfR aptamer would not cross-react with the HEY cells. This would confirm that the specific binding (FIG. 10) and internalisation seen by the conjugate aptamers against the HEY cell line could be attributed to the EpCAM-binding portion of the aptamers. This was done by two methods, with the tightest binding anti-TfR aptamer, TfR3. A binding curve was generated via flow cytometry and the cells were visualised with confocal microscopy.

Figure 10:
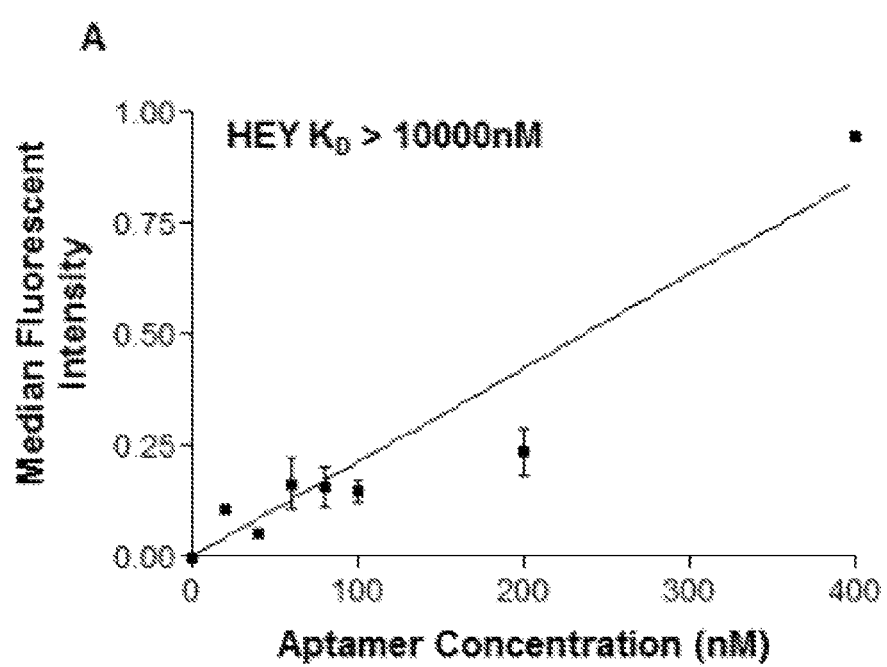
FIG. 10 shows incubation of TfR aptamer with EpCAM-positive cell line (HEY). The aptamer TfR3 was incubated with HEY cells and analysed using (A) flow cytometry (Binding curves obtained using concentrations 0, 20, 40, 60, 80, 100, 200 and 400 nM. Data presented as median±SEM (n=3)). Results demonstrate clear non-specific binding.

The binding assay results of TfR3 against the HEY cell line showed clear non-specific binding (FIG. 10). In concordance with this finding, internalisation of the aptamer was not detected in these same cells. These two lines of evidence provide confidence in the EpCAM-binding properties of the conjugate aptamers.

Example 4 An In Vitro Blood Brain Barrier Model (i) Characterisation of the In Vitro BBB Model The purpose of designing an aptamer for the targeting of TfR was to enable it to pass through the BBB endothelial monolayer. A recognised method to assess the permeability of a substance across the BBB is to produce an in vitro model of this system (Wuest D M et al (2013) Journal of Neuroscience Methods 212(2):211-21). As such, bEnd.3 cells were subcultured and seeded on transwell inserts in serum-free media with the intention of growing a tight monolayer of endothelial cells. The integrity of this barrier was assessed by measuring the transendothelial electrical resistance (TEER) as described (Wilhelm I et al (2011) Acta Neurobiologiae Experimentalis 71(1):113-28). The transwells inserts were stained with haematoxylin and eosin and imaged via light microscopy. The images of the transwells showed a patchy coverage of cells, consistent with the lower TEER reading. Despite this, however, the coverage of cells across the membrane was extensive.

(ii) Determination of Conjugate Aptamer Permeability Across an In Vitro Blood Brain Barrier Model The key characteristic that was required of the conjugate aptamers in order for them to be used in the targeting of brain metastases is the ability to cross the BBB. The best way to do that in an in vitro setting is to determine if these aptamers can pass through a model of this physiological system. Therefore, HEY cells were co-cultured in the bottom compartment of an in vitro BBB model, and after being allowed to grow overnight, 2 µM of the conjugate aptamers were incubated in the upper compartment for three hours. HEY cells were subsequently visualised via confocal microscopy.

Two of the conjugate aptamers, Bi2 and Bi3 were observed to become internalised into the HEY cells (not shown). These are the same two aptamers that demonstrated specific binding to the bEnd.3 cell line. In contrast, Bi1 was not observed inside HEY cells after having been incubated on the other side of a bEnd.3 endothelial monolayer. This is an interesting observation, given that this aptamer had previously been observed to internalise into HEY cells, but not bEnd.3 cells. This provides a possible indication that the Bi1 aptamer did not pass through the in vitro model, thus supporting the suggestion that the other two aptamers crossed the membrane via RMT.

Figure 11:
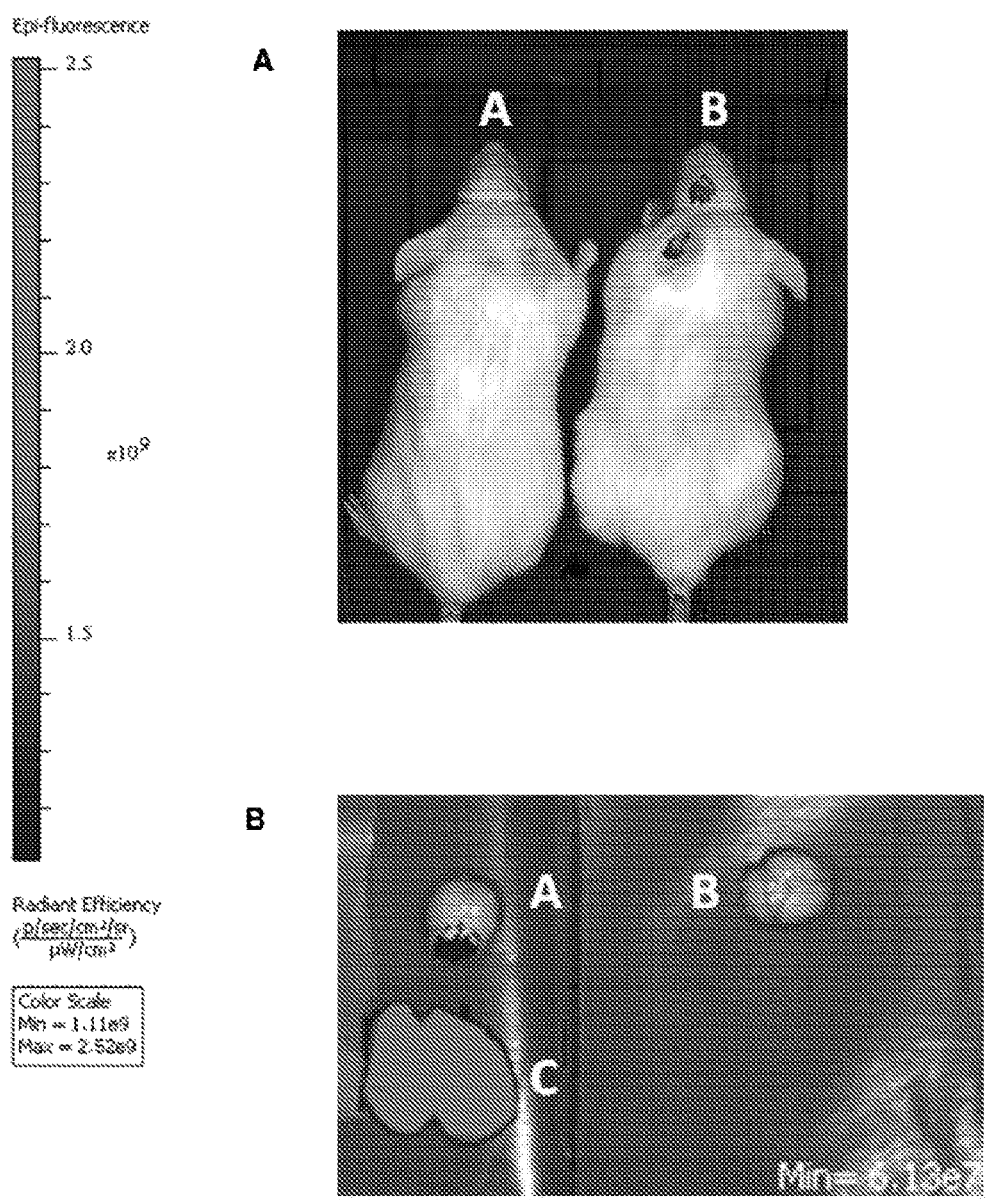
FIG. 11 shows whole body fluorescent images (A) of mice injected with 2 nmoles of aptamer Bi1 or aptamer 6 (a conjugate of Bi3 and Bi1) injected via tail vein and fluorescent images of brain and liver (B). Brain (BA) of a mouse injected with aptamer 6, liver (BC) of a mouse injected with aptamer 6 and brain (BB) of mouse injected with aptamer 1.

Example 5 Determination of Conjugate Aptamer Permeability Across the Blood Brain Barrier In Vivo Mice were injected with fluorescently labelled aptamer Bi1 (negative control) and aptamer 6 which was a combination of the TfR binding portion of aptamer Bi3 attached to the EpCAM binding portion of Bi1 and has the sequence 5'-GC GCG GTA C CG CGC TA ACG G AT TCC TTT T CC GT-3' (SEQ ID NO:10) with an inverted dT at the 3' end and fluorophore at the 5' end. When 2 nmole of aptamer 6 was injected into the tail vein of a healthy mouse, a signal was distinguishable in the head region with 10 minutes using a Xenogen IVIS Lumina II imaging system as shown in FIG. 11A. The fluorescent signal strength of negative aptamer Bi1 was $6.82 \times 10^9$ and $1.25 \times 10^{10}$ for EpCAM aptamer 6.

When the mouse was euthanized at 30 minutes and the dissected brain imaged, a clear signal could be seen on the periphery of the brain, in contrast to no signal observed in mice injected with negative control Aptamer Bi1. These results demonstrate that aptamers can effectively be used as blood brain barrier transcytosing agents. The high level of TfR expression in the liver suggests a particular role for this receptor in the capture and storage of iron. Liver is known to express the transferrin receptor.

Example 6 Transferrin/EpCAM Aptamer Uptake in Brain

To evaluate the advantage of positive transferrin-modified aptamers over their negative transferrin-modified counterparts in brain uptake, the biodistribution of aptamers with four various structures (transferrin+/EpCAM+, transferrin+/EpCAM−, transferrin−/EpCAM+, transferrin−/EpCAM−) were studied at 30 min and 60 min after a single i.v. injection of these agents at a dosage of 40 nmol/Kg into NOD/SCID mice.

The Various Aptamers were Designated as Follows:

```
TEPP: transferrin positive EpCAM positive aptamer
Bi3
                                        (SEQ ID NO: 3)
TENN: transferrin negative, EpCAm negative aptamer
Bi1
                                        (SEQ ID NO: 1)
TEPN: transferrin positive, EpCAM negative aptamer
5' GC GCG GTA C CG CGC TA ACG G AT TCC TTT T CC
GT 3'
TENP: transferrin negative, EpCAM positive aptamer
5' GC GCG TGC A CG CGC TA ACG G AG GTT GCG TCC
GT 3'
```

Figures 1, 12:
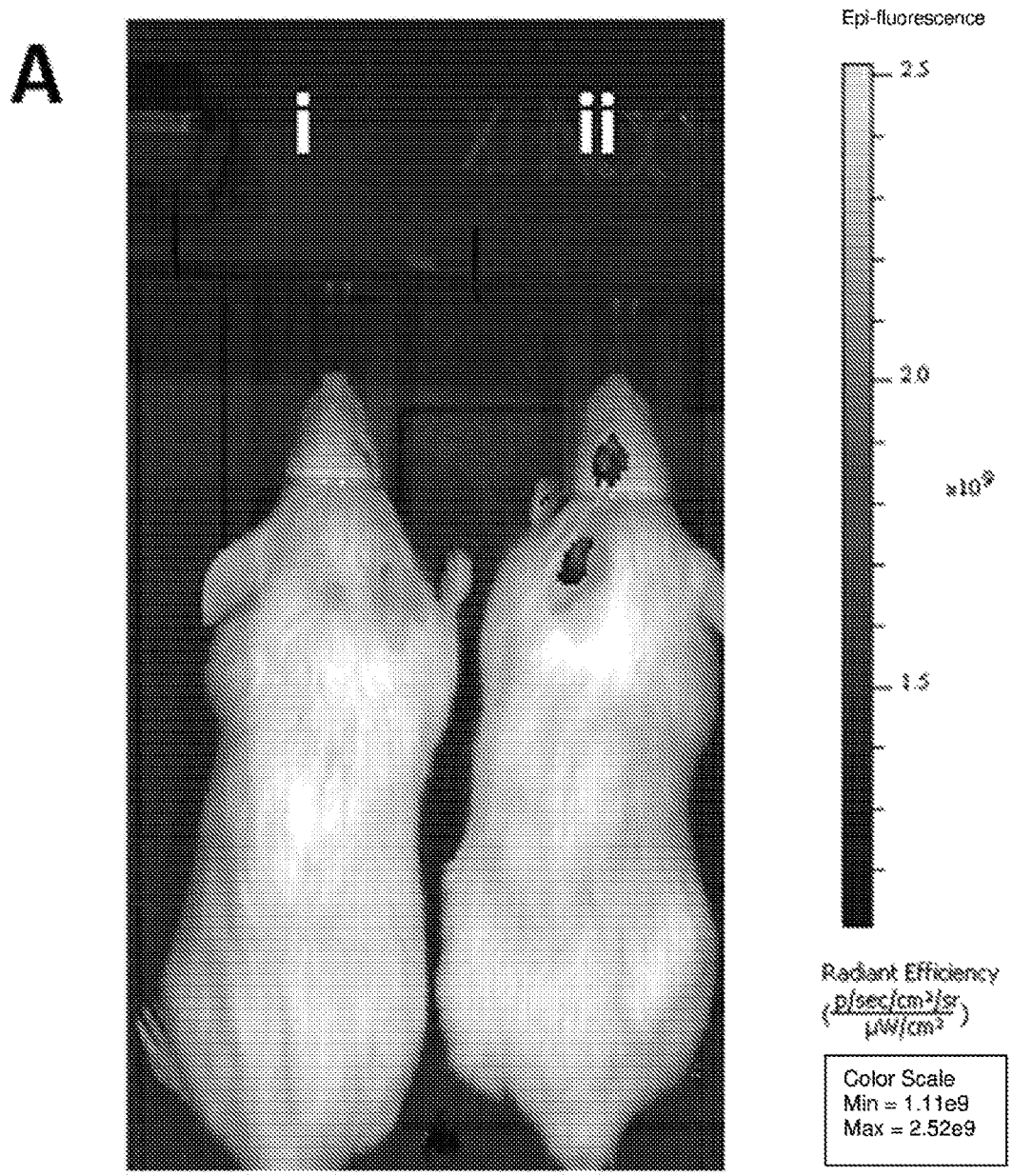
Figure 12:
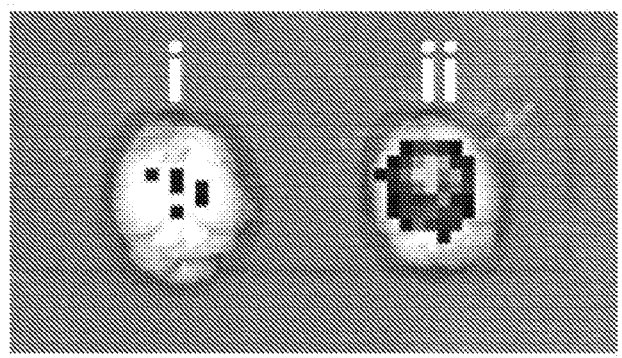
Figure 2:
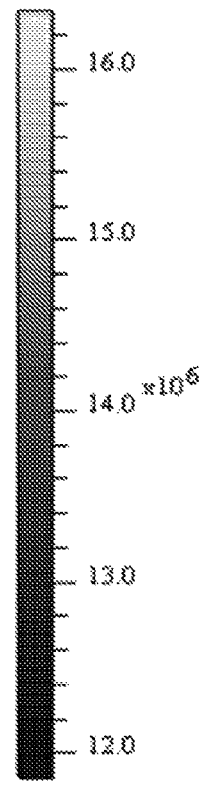
Figure 13:
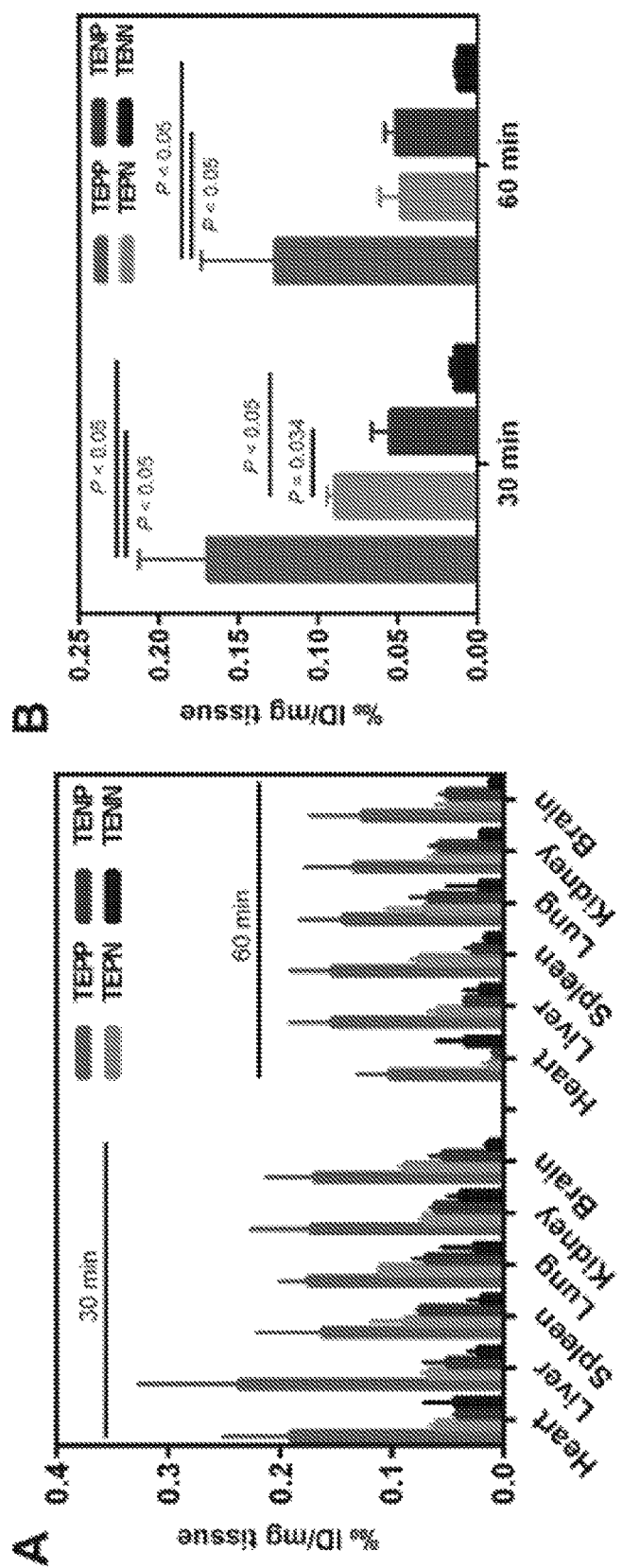
FIG. 13 shows biodistribution of transferrin/EpCAM aptamer in brain. NOD/SCID mice received a single i.v. injection of 40 nmol/Kg of transferrin/EpCAM aptamer with four various structures (TEPP: Bi3 transferrin$^+$/EpCAM$^+$; TEPN: transferrin$^+$/EpCAM$^-$; TENP: transferrin$^-$/EpCAM$^+$; TENN: Bi1 transferrin$^-$/EpCAM$^-$). The concentration of aptamers, expressed as % of injected dose (ID) per mg of tissue, in tissues indicated was determined at 30 min and 60 min after the agent administration using ELISA. Data are means±SEM (n=3).

With regard to the accumulation in brains, the amount of transferrin+/EpCAM+ was statistically significantly higher than that of the transferrin−/EpCAM− (or transferrin−/EpCAM+) counterpart at 30 min and 60 min with a 12.2-fold (or 3.1-fold) and 10.8-fold (or 2.5-fold) higher, respectively (FIG. 12 and FIG. 13). Furthermore, there was statistically significantly higher levels of transferrin+/EpCAM− uptake in brain than that of transferrin−/EpCAM− after 30 min administration, while no gross difference was found between these two groups following 1 h injection. These data are consistent with the sustained retention of transferrin+/EpCAM+ aptamer over transferrin−/EpCAM− in the brain at 1 h post-injection through the in vivo live imaging, indicating that the transferrin+modified aptamer could be retained in the brain at a high concentration in vivo for at least 1 h. Taken together, the transferrin+ modified aptamer exhibited a favourable accumulation and retention profile compared to that of the negative transferrin-modified aptamer in brain, suggesting this aptamer could be developed as effective modality for overcoming the brain-blood-barrier, thereby opening a new window for targeted drug delivery to brain.

The invention claimed is:

1. An isolated bifunctional aptamer conjugate comprising:
   (i) the sequence 5'-GCG CGG TAC CGC GCT AAC GGA GGT TGC GTC CGT-3' (SEQ ID NO:3); or
   (ii) the sequence of SEQ ID NO:3 having one to five substitutions therein, wherein the aptamer conjugate binds to EpCAM and TfR.

2. The aptamer conjugate according to claim 1 having a sequence length between 33 and 100 bases.

3. The aptamer conjugate according to claim 1, wherein the aptamer has a binding affinity (KD) for EpCAM of between 5 nM and 100 nM.

4. The aptamer conjugate according to claim 1, which consists of the sequence 5'-GCG CGG TAC CGC GCT AAC GGA GGT TGC GTC CGT-3' (SEQ ID NO:3).

5. The aptamer conjugate according to claim 1 comprising one or more modifications that improve aptamer stability in vitro or in vivo.

6. The aptamer conjugate according to claim 1 which further comprises a chemotherapeutic agent intercalated into the stem region(s) of the aptamer conjugate.

7. The aptamer conjugate according to claim 6, wherein the chemotherapeutic agent is doxorubicin.

8. The aptamer conjugate according to claim 7, wherein the aptamer has a binding affinity (KD) for TfR of about 300 to 340 nM and a binding affinity (KD) for EpCAM of about 210 to 220 nM.

9. A diagnostic agent comprising the aptamer conjugate according to claim 1 coupled to a detectable label.

10. An anticancer agent comprising the aptamer conjugate according to claim 1 coupled to a moiety selected from a toxin, radionuclides or chemotherapeutic agent.

11. A method for identifying an EpCAM expressing cell(s) and/or cancer stem cell(s) in a subject or in a biological sample obtained from a subject having, or suspected of having brain cancer or a brain tumour or metastasis, the method comprising contacting the cell or sample with the aptamer conjugate according to claim 1, or the diagnostic agent according to claim 9.

12. A method for treating or preventing a brain cancer or tumour in a subject, or a brain metastasis in a subject, comprising providing a subject with the aptamer conjugate according to claim 1, or the anticancer agent according to claim 10.

13. A composition comprising a therapeutically effective amount of the aptamer conjugate according to claim 1, or the anticancer agent according to claim 9, together with a pharmaceutically acceptable carrier and/or excipient.

14. The aptamer conjugate according to claim 1 which binds to TfR independently of binding to EpCAM.

* * * * *

UNITED STATES PATENT AND TRADEMARK OFFICE
CERTIFICATE OF CORRECTION

PATENT NO. : 10,577,610 B2  
APPLICATION NO. : 15/550671  
DATED : March 3, 2020  
INVENTOR(S) : Sarah Shigdar Page 1 of 1

It is certified that error appears in the above-identified patent and that said Letters Patent is hereby corrected as shown below:

On the Title Page

Item [71], should read:
--Deakin University, Waurn Ponds (AU)--

Item [72], should read:
--Sarah Shigdar, Waurn Ponds (AU)--

Signed and Sealed this
Twenty-ninth Day of September, 2020

Andrei Iancu
*Director of the United States Patent and Trademark Office*

SEQUENCE LISTING

```
<160> NUMBER OF SEQ ID NOS: 18

<210> SEQ ID NO 1
<211> LENGTH: 33
<212> TYPE: DNA
<213> ORGANISM: Artificial Sequence
<220> FEATURE:
<223> OTHER INFORMATION: consensus DNA sequence of aptamer conjugate
<220> FEATURE:
<221> NAME/KEY: misc_feature
<222> LOCATION: (7)..(8)
<223> OTHER INFORMATION: n is a, t, c or g
<220> FEATURE:
<221> NAME/KEY: misc_feature
<222> LOCATION: (33)..(33)
<223> OTHER INFORMATION: n is t  or 3' inverted deoxythymidine (dT)

<400> SEQUENCE: 1
gcgcggnncc gcgctaacgg aggttgcgtc cgn                               33

<210> SEQ ID NO 2
<211> LENGTH: 33
<212> TYPE: DNA
<213> ORGANISM: Artificial Sequence
<220> FEATURE:
<223> OTHER INFORMATION: DNA sequence of aptamer conjugate Bi2
<220> FEATURE:
<221> NAME/KEY: misc_feature
<222> LOCATION: (33)..(33)
<223> OTHER INFORMATION: n is t or 3' inverted deoxythymidine (dT)

<400> SEQUENCE: 2
gcgcgggccc gcgctaacgg aggttgcgtc cgn                               33

<210> SEQ ID NO 3
<211> LENGTH: 33
<212> TYPE: DNA
```

<213> ORGANISM: Artificial Sequence
<220> FEATURE:
<223> OTHER INFORMATION: DNA sequence of aptamer conjugate Bi3
<220> FEATURE:
<221> NAME/KEY: misc_feature
<222> LOCATION: (33)..(33)
<223> OTHER INFORMATION: n is t or 3' inverted deoxy thymidine (dT)

<400> SEQUENCE: 3
gcgcggtacc gcgctaacgg aggttgcgtc cgn            33

<210> SEQ ID NO 4
<211> LENGTH: 14
<212> TYPE: DNA
<213> ORGANISM: Artificial Sequence
<220> FEATURE:
<223> OTHER INFORMATION: DNA sequence of aptamer TfR1

<400> SEQUENCE: 4
gcgtgtgcac acgc            14

<210> SEQ ID NO 5
<211> LENGTH: 14
<212> TYPE: DNA
<213> ORGANISM: Artificial Sequence
<220> FEATURE:
<223> OTHER INFORMATION: DNA sequence of aptamer TfR2

<400> SEQUENCE: 5
gcgtgggccc acgc            14

<210> SEQ ID NO 6
<211> LENGTH: 14
<212> TYPE: DNA
<213> ORGANISM: Artificial Sequence
<220> FEATURE:
<223> OTHER INFORMATION: DNA sequence of aptamer TfR3

<400> SEQUENCE: 6
gcgtggtacc acgc            14

<210> SEQ ID NO 7
<211> LENGTH: 14
<212> TYPE: DNA
<213> ORGANISM: Artificial Sequence
<220> FEATURE:
<223> OTHER INFORMATION: DNA sequence of aptamer TfR4

<400> SEQUENCE: 7
gcgtggtcac acgc            14

<210> SEQ ID NO 8
<211> LENGTH: 33
<212> TYPE: DNA
<213> ORGANISM: Artificial Sequence
<220> FEATURE:
<223> OTHER INFORMATION: DNA sequence of aptamer conjugate Bi1
<220> FEATURE:
<221> NAME/KEY: misc_feature
<222> LOCATION: (33)..(33)
<223> OTHER INFORMATION: n is t or 3' inverted deoxythymidine (dT)

<400> SEQUENCE: 8
gcgcgtgcac gcgctaacgg attccttttc cgn            33

<210> SEQ ID NO 9
<211> LENGTH: 17

```
<212> TYPE: DNA
<213> ORGANISM: Artificial Sequence
<220> FEATURE:
<223> OTHER INFORMATION: DNA sequence of aptamer Ep7
<220> FEATURE:
<221> NAME/KEY: misc_feature
<222> LOCATION: (17)..(17)
<223> OTHER INFORMATION: n is t or 3' inverted deoxythymidine (dT)

<400> SEQUENCE: 9
acagaggttg cgtctgn                                                17

<210> SEQ ID NO 10
<211> LENGTH: 33
<212> TYPE: DNA
<213> ORGANISM: Artificial Sequence
<220> FEATURE:
<223> OTHER INFORMATION: DNA sequence of aptamer conjugate (aptamer 6)
<220> FEATURE:
<221> NAME/KEY: misc_feature
<222> LOCATION: (33)..(33)
<223> OTHER INFORMATION: n is t or 3' inverted deoxythymidine (dT)

<400> SEQUENCE: 10
gcgcggtacc gcgctaacgg attccttttc cgn                              33

<210> SEQ ID NO 11
<211> LENGTH: 16
<212> TYPE: DNA
<213> ORGANISM: Artificial Sequence
<220> FEATURE:
<223> OTHER INFORMATION: synthetic sequence

<400> SEQUENCE: 11
cccacgttgt catggg                                                 16

<210> SEQ ID NO 12
<211> LENGTH: 12
<212> TYPE: DNA
<213> ORGANISM: Artificial Sequence
<220> FEATURE:
<223> OTHER INFORMATION: synthetic sequence

<400> SEQUENCE: 12
ggggttggcc cc                                                     12

<210> SEQ ID NO 13
<211> LENGTH: 29
<212> TYPE: DNA
<213> ORGANISM: Artificial Sequence
<220> FEATURE:
<223> OTHER INFORMATION: synthetic sequence

<400> SEQUENCE: 13
cgcgcgccgc aggttgcgtg cggcgcgcg                                   29

<210> SEQ ID NO 14
<211> LENGTH: 29
<212> TYPE: DNA
<213> ORGANISM: Artificial Sequence
<220> FEATURE:
<223> OTHER INFORMATION: synthetic sequence

<400> SEQUENCE: 14
cgcgcgccgc attccttttg cggcgcgcg                                   29

<210> SEQ ID NO 15
```

```
<211> LENGTH: 64
<212> TYPE: DNA
<213> ORGANISM: Artificial Sequence
<220> FEATURE:
<223> OTHER INFORMATION: synthetic sequence TfR apatmer

<400> SEQUENCE: 15
gaattccgcg tgtgcacacg ctcacagtta gtatcgctac gttctttggt agtccgttcg        60
ggat                                                                     64

<210> SEQ ID NO 16
<211> LENGTH: 48
<212> TYPE: DNA
<213> ORGANISM: Artificial Sequence
<220> FEATURE:
<223> OTHER INFORMATION: synethetic sequence EpCAM aptamer

<400> SEQUENCE: 16
cactacagag gttgcgtctg tcccacgttg tcatgggggg ttggcctg                     48

<210> SEQ ID NO 17
<211> LENGTH: 50
<212> TYPE: DNA
<213> ORGANISM: Artificial Sequence
<220> FEATURE:
<223> OTHER INFORMATION: synthetic sequence TfR aptamer

<400> SEQUENCE: 17
gcgtgtgcac acggtcactt agtatcgcta cgttctttgg ttccgttcgg                   50

<210> SEQ ID NO 18
<211> LENGTH: 14
<212> TYPE: DNA
<213> ORGANISM: Artificial Sequence
<220> FEATURE:
<223> OTHER INFORMATION: synthetic sequence TfR aptamer

<400> SEQUENCE: 18
gcgtgtgcac acgg                                                          14
```